United States Patent
Stucki et al.

(10) Patent No.: US 8,663,299 B2
(45) Date of Patent: Mar. 4, 2014

(54) INTERNAL CABLE FIXATOR

(75) Inventors: Simon Stucki, Thun (CH); Guido Hertig, Burgdorf (CH)

(73) Assignee: Depuy Synthes Products, LLC, Raynham, MA (US)

( * ) Notice: Subject to any disclaimer, the term of this patent is extended or adjusted under 35 U.S.C. 154(b) by 812 days.

(21) Appl. No.: 12/813,019

(22) Filed: Jun. 10, 2010

(65) Prior Publication Data
US 2010/0318137 A1    Dec. 16, 2010

Related U.S. Application Data

(60) Provisional application No. 61/186,141, filed on Jun. 11, 2009.

(51) Int. Cl.
*A61B 17/84*    (2006.01)
(52) U.S. Cl.
USPC ................. 606/324; 24/135 R; 24/136 R
(58) Field of Classification Search
USPC .......... 24/115 R, 122.3, 122.6, 129 C, 131 R, 24/136 L, 136 R, 135 R, 136 B, 132 AA; 104/200–201; 606/74, 263, 277, 324
See application file for complete search history.

(56) References Cited

U.S. PATENT DOCUMENTS

| | | | | |
|---|---|---|---|---|
| 2,565,605 A | * | 8/1951 | Grayson | 24/114.5 |
| 2,634,474 A | * | 4/1953 | Grayson | 403/206 |
| 3,163,904 A | * | 1/1965 | Ziolkowski | 403/365 |
| 4,127,119 A | | 11/1978 | Kronner | |
| 5,170,537 A | * | 12/1992 | Sperling | 24/136 A |
| 5,415,658 A | * | 5/1995 | Kilpela et al. | 606/300 |
| 6,338,167 B1 | | 1/2002 | Baker et al. | |
| 6,488,317 B1 | * | 12/2002 | Daoud | 285/322 |
| 7,172,595 B1 | * | 2/2007 | Goble | 606/86 A |
| 8,225,463 B2 | * | 7/2012 | Bourke et al. | 24/132 AA |
| 8,241,288 B2 | * | 8/2012 | Justin et al. | 606/74 |
| 2006/0195104 A1 | | 8/2006 | Schlafli et al. | |
| 2007/0010817 A1 | | 1/2007 | de Coninck | |

FOREIGN PATENT DOCUMENTS

EP    0 517 939    12/1992

* cited by examiner

*Primary Examiner* — Nicholas Woodall
*Assistant Examiner* — Larry E Waggle, Jr.
(74) *Attorney, Agent, or Firm* — Fay Kaplun & Marcin, LLP

(57) ABSTRACT

A cable fixation device comprises a clamp including a head portion and a body portion along with a lumen extending therethrough. The head portion is removably coupleable with an actuating mechanism. The lumen is sized and shaped to slidably accommodate a cable in combination with a clamping ring including a channel extending therethrough. The channel includes a first portion and a second portion. The first portion is sized and shaped to slidably accommodate the cable therethrough. The second portion is sized and shaped to engage the clamp. A portion of the clamp is movable between a first configuration and a second configuration, the cable slidable therethrough in the first configuration. The portion of the clamp moves radially inward in the second configuration to clamp the cable.

11 Claims, 33 Drawing Sheets

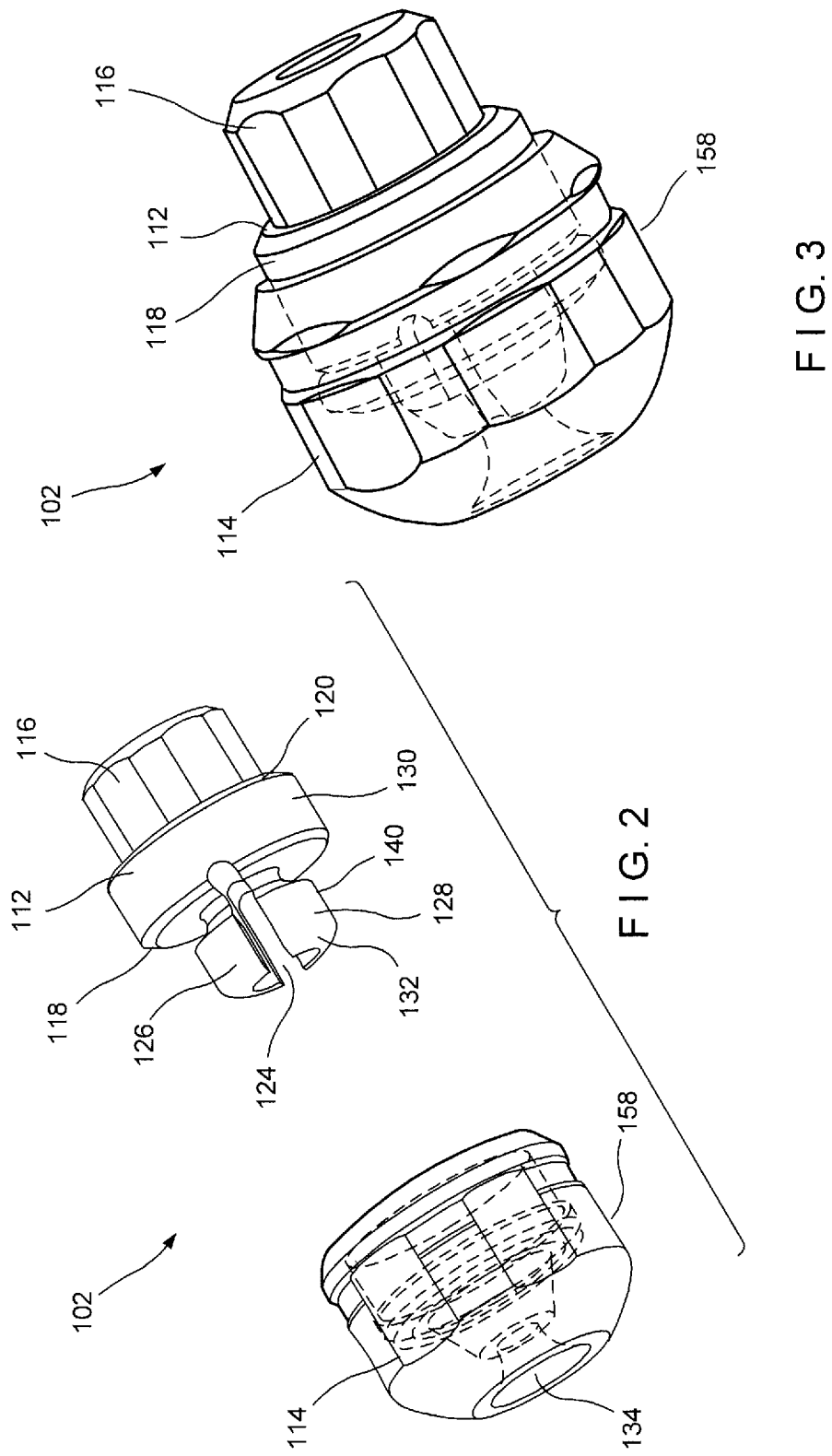

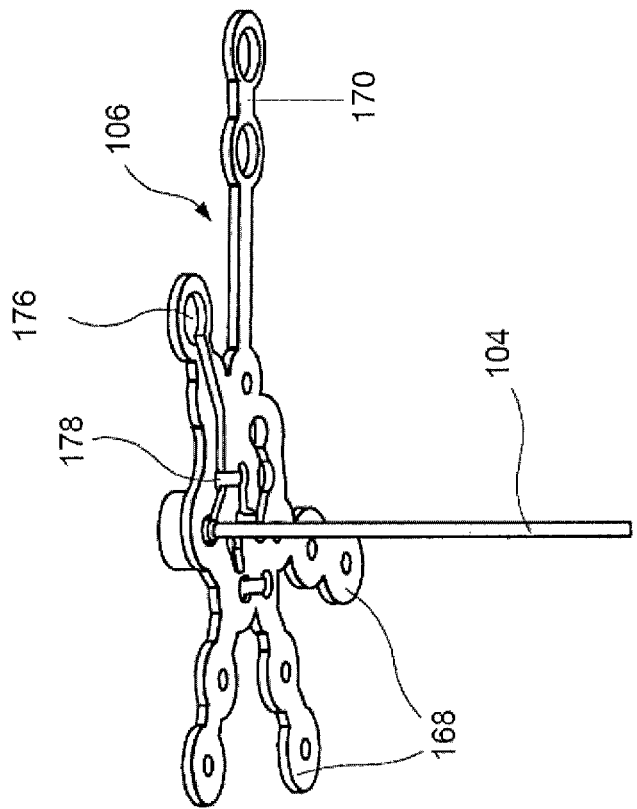
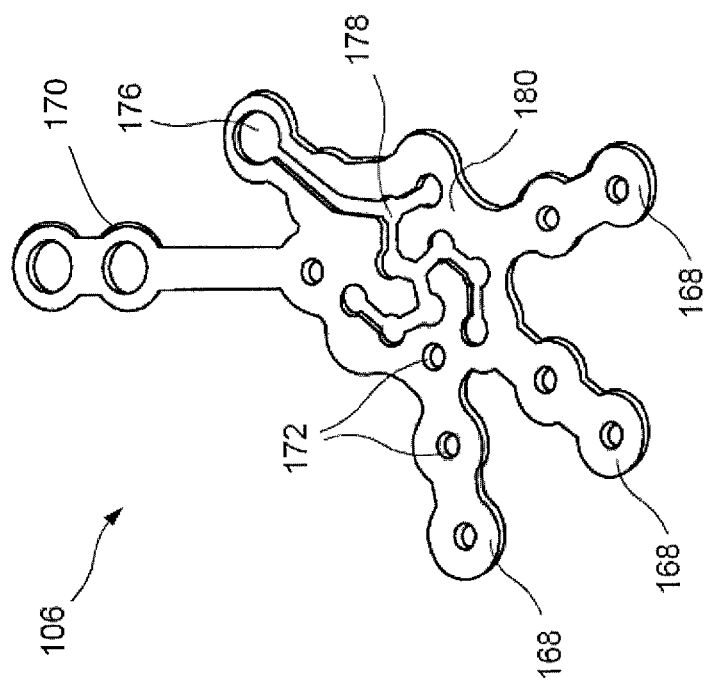

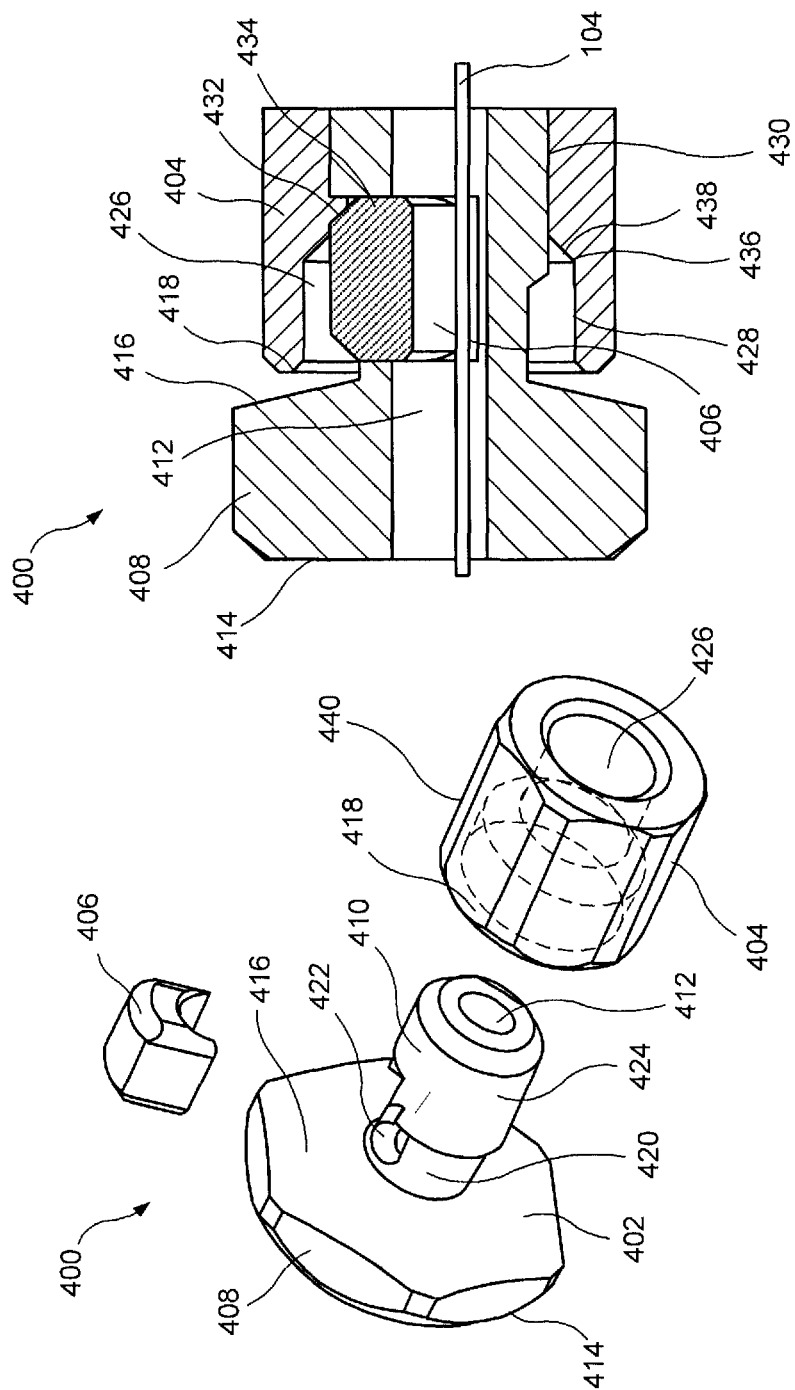

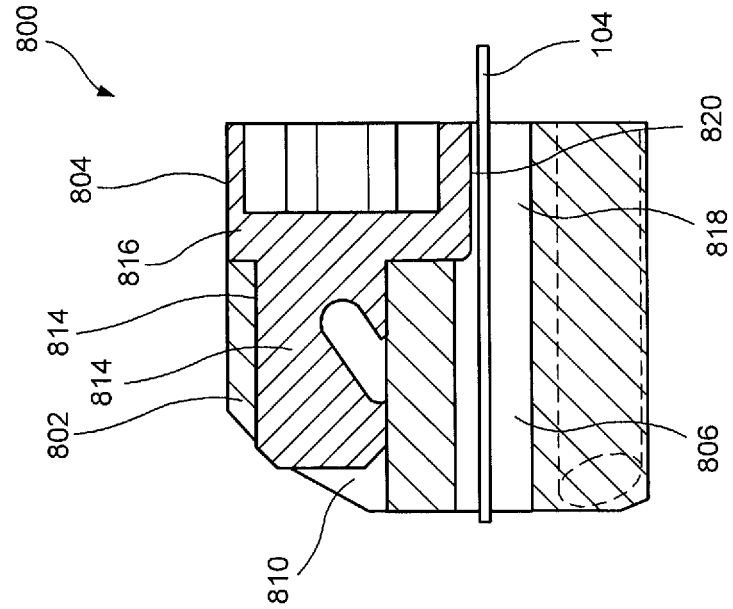
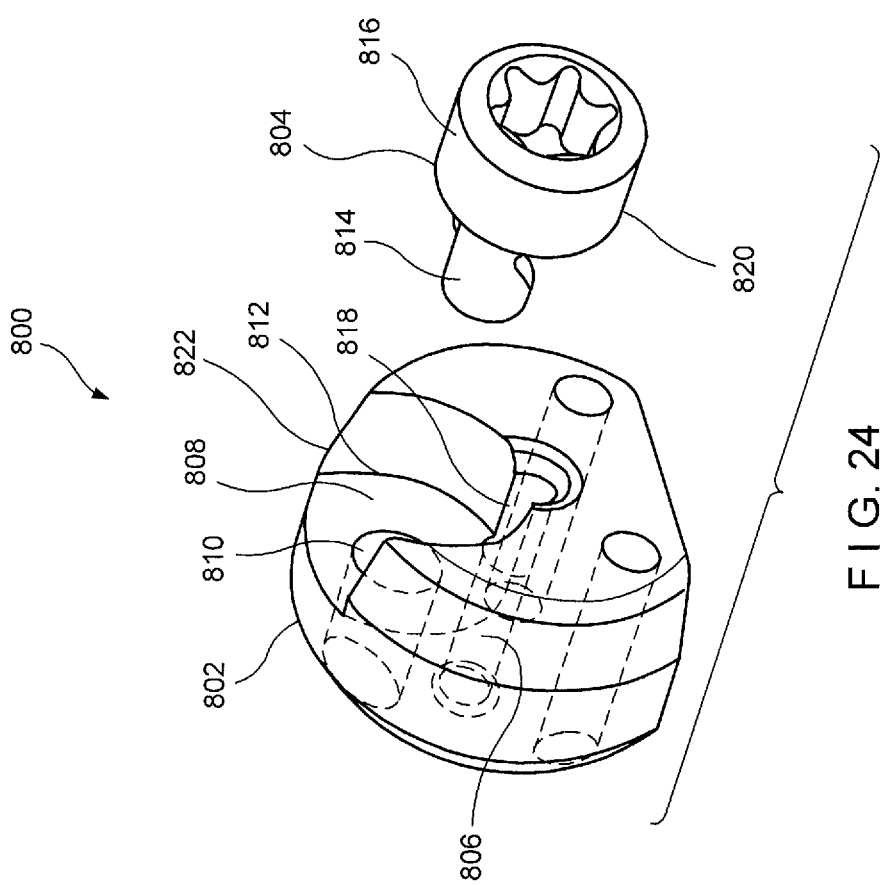
FIG. 25
FIG. 24

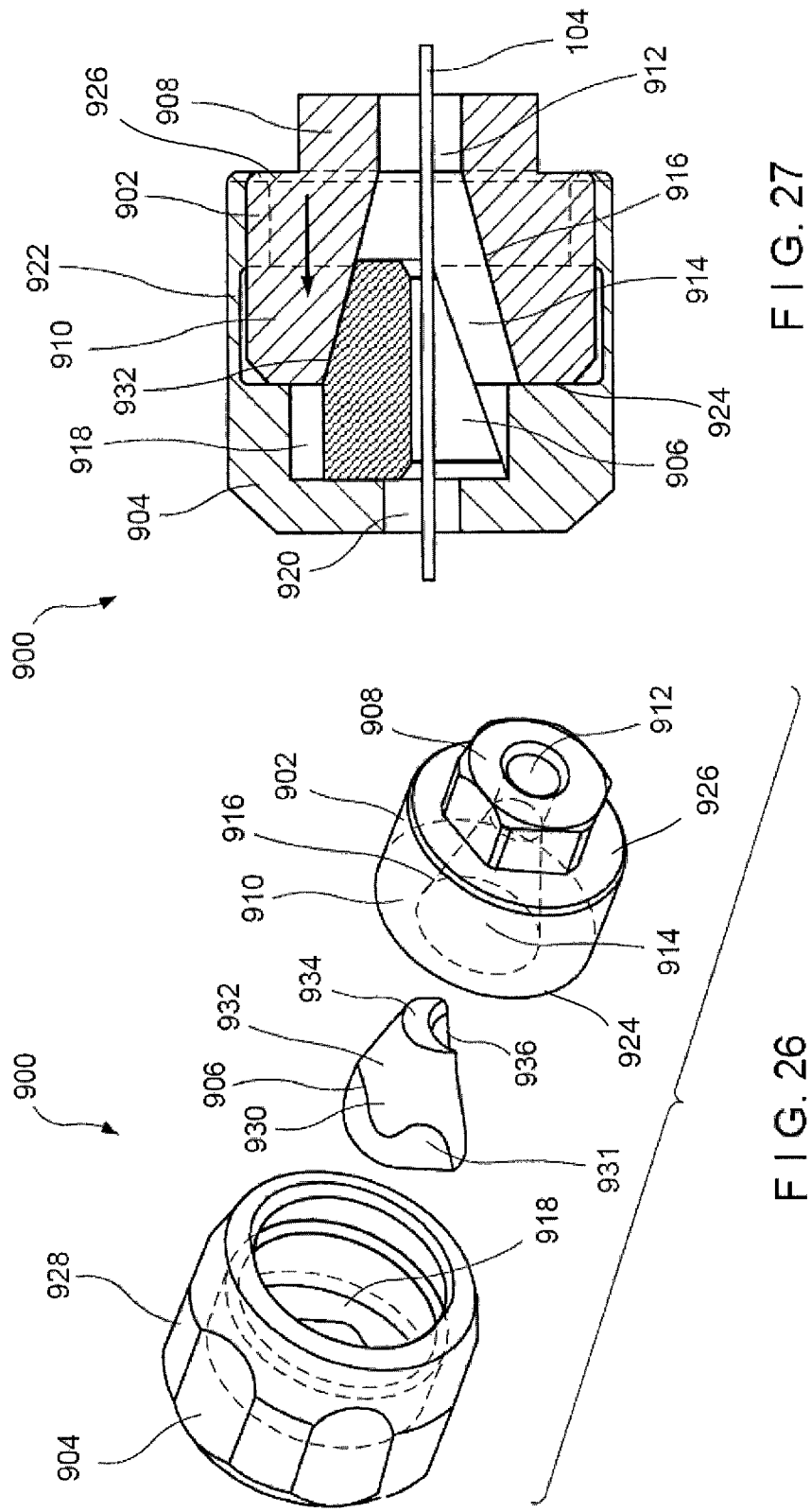

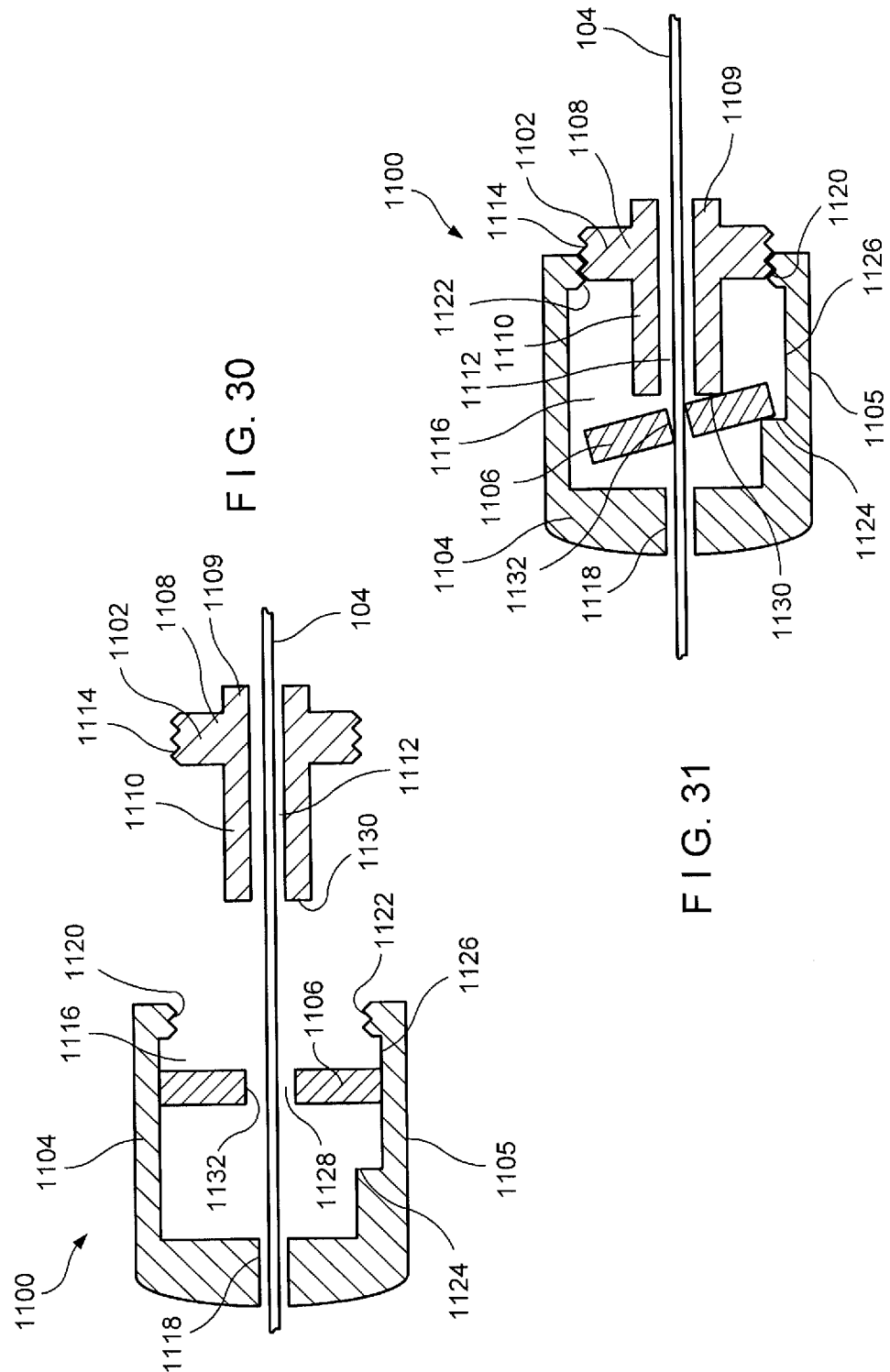

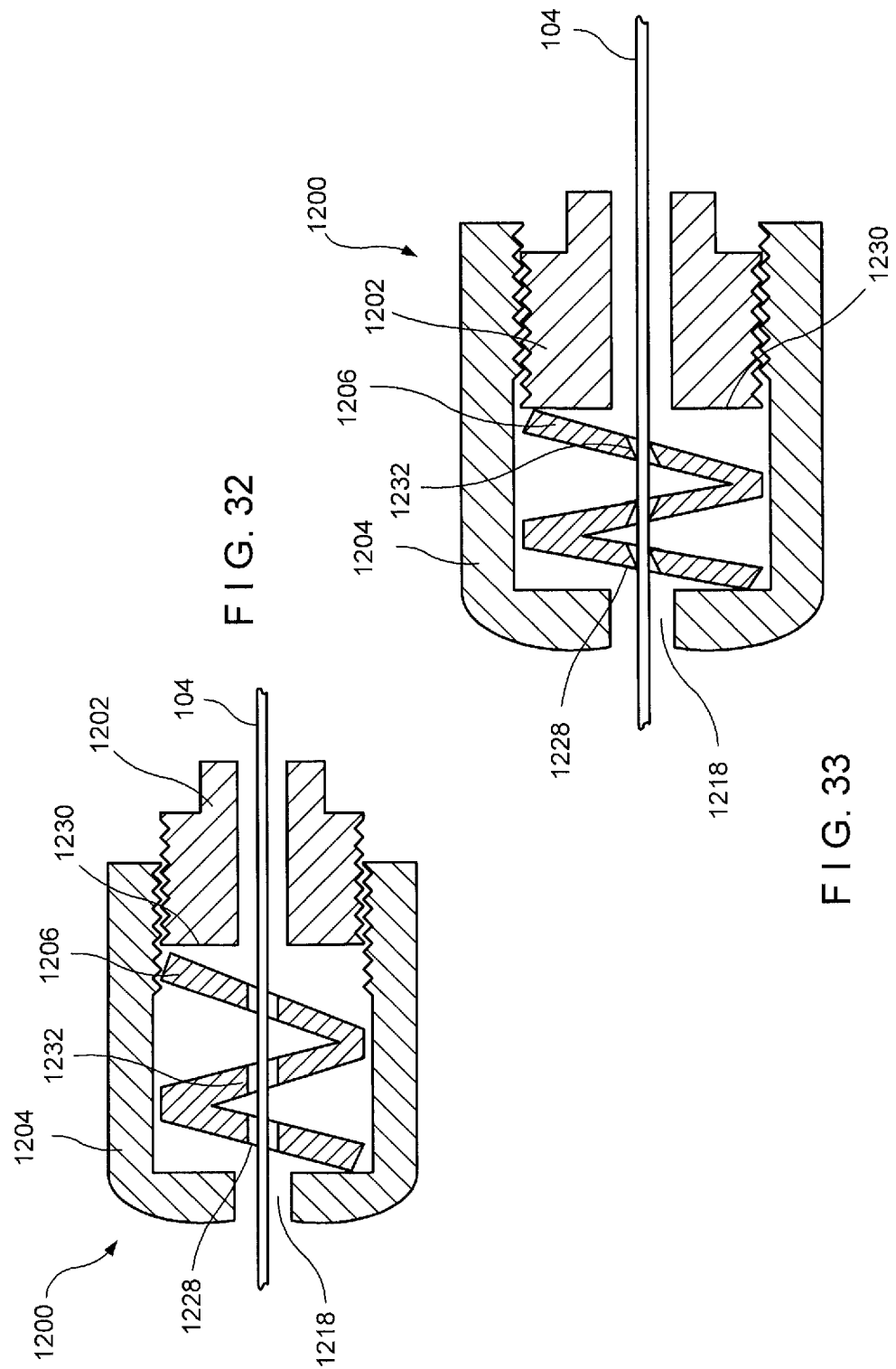

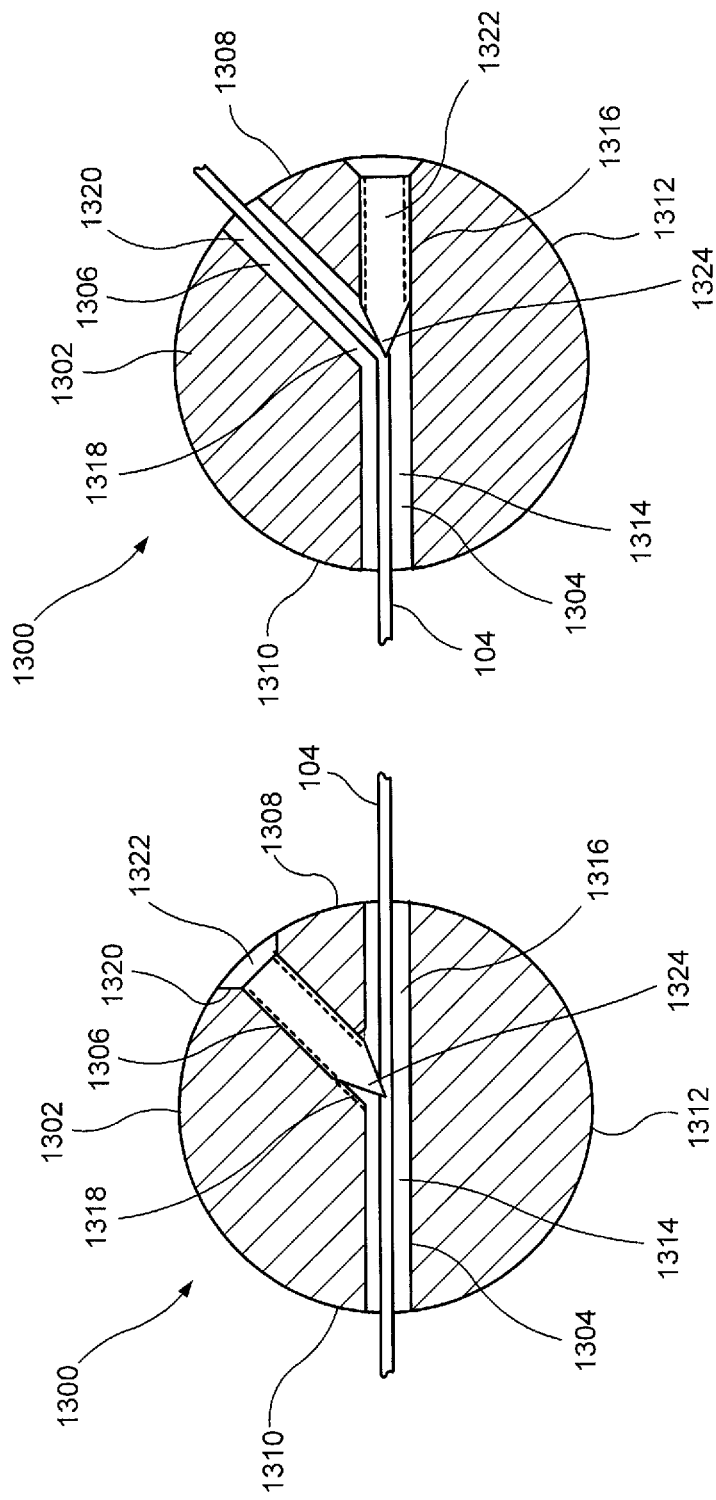

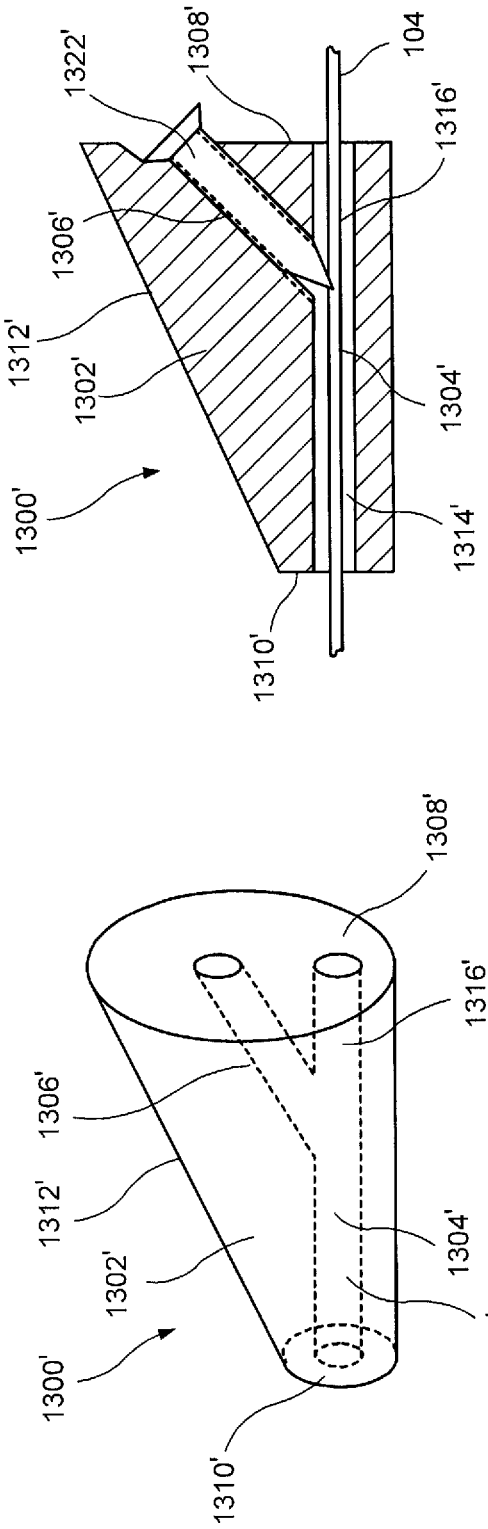
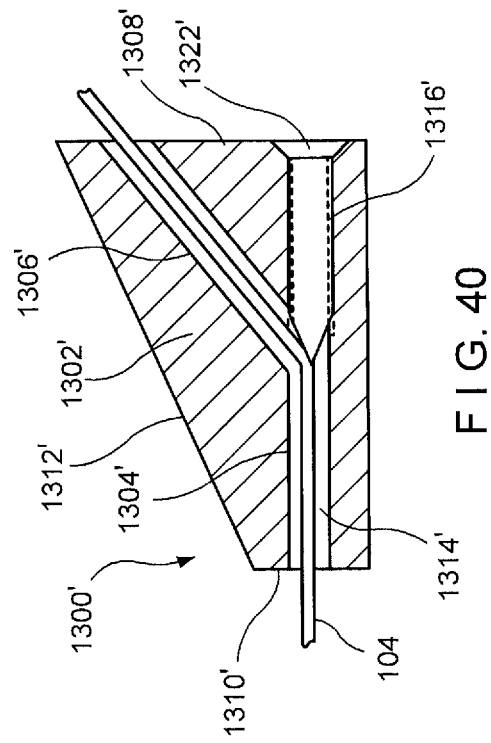

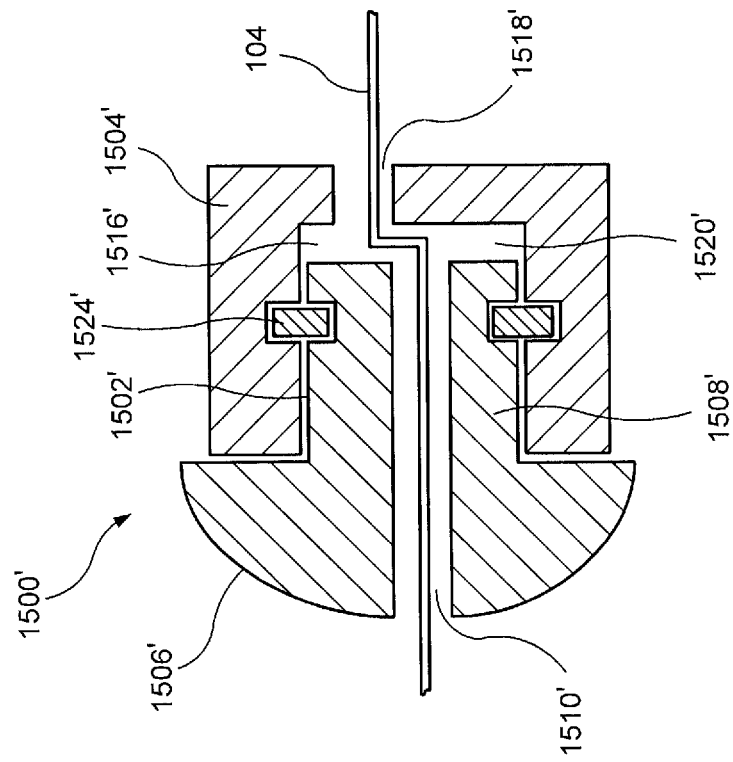
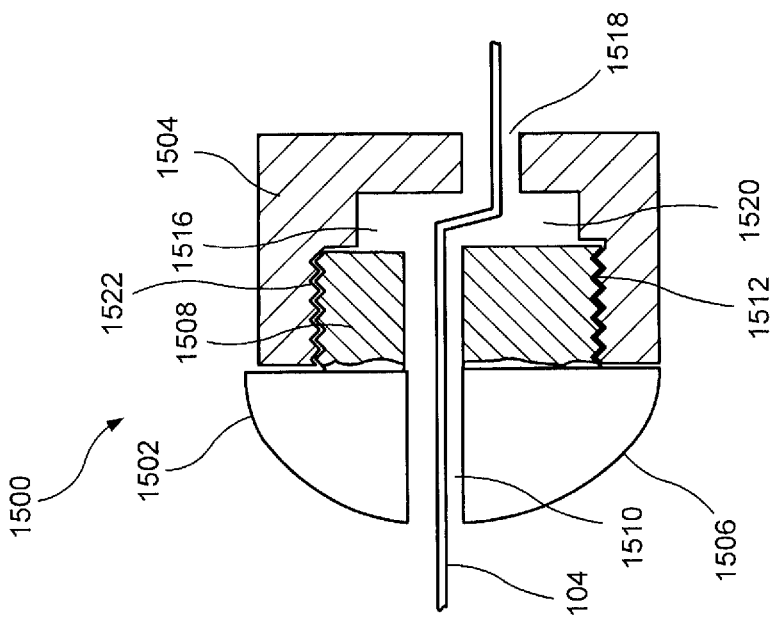
FIG. 44
FIG. 43

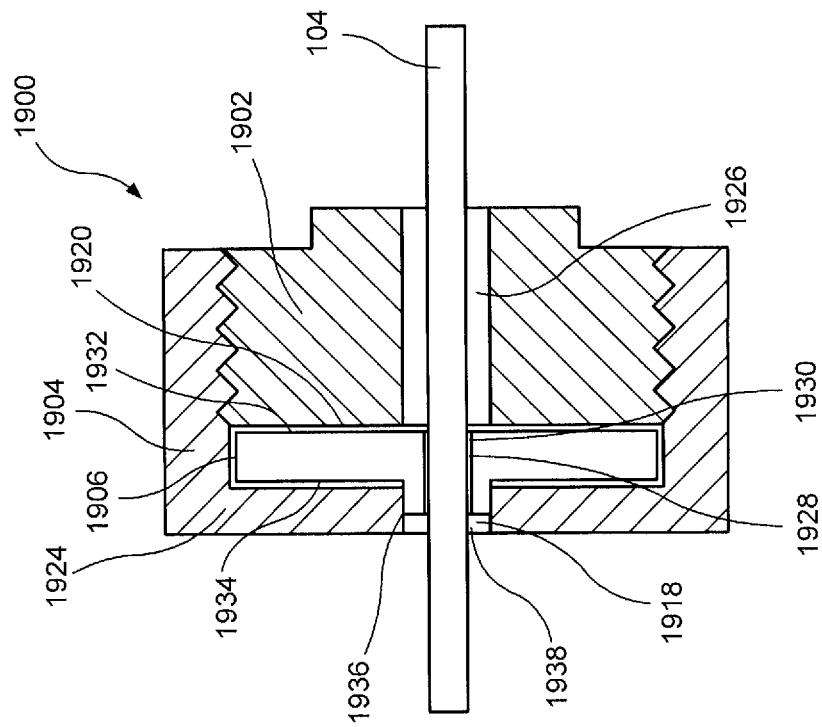
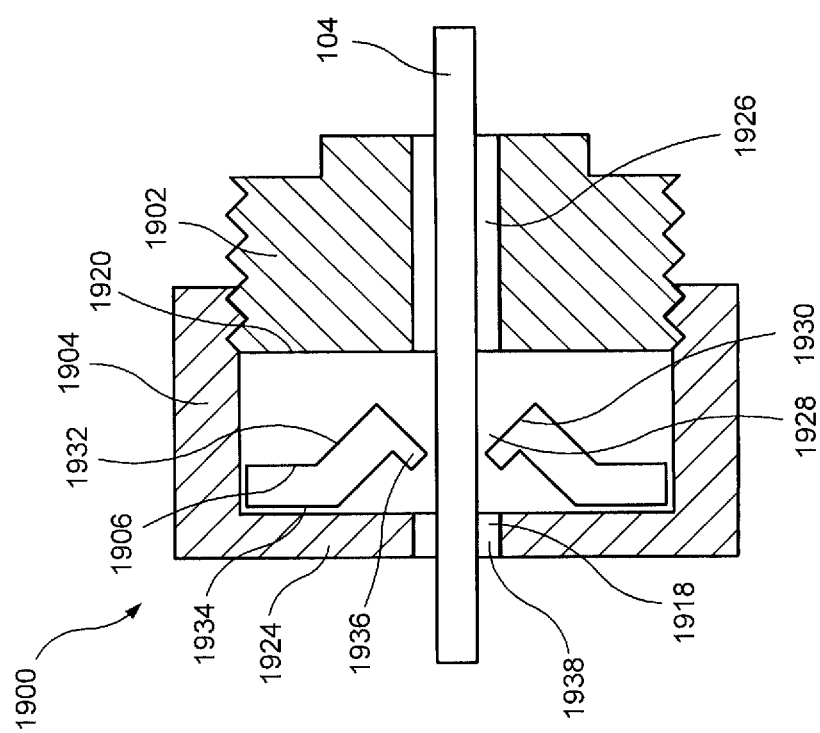

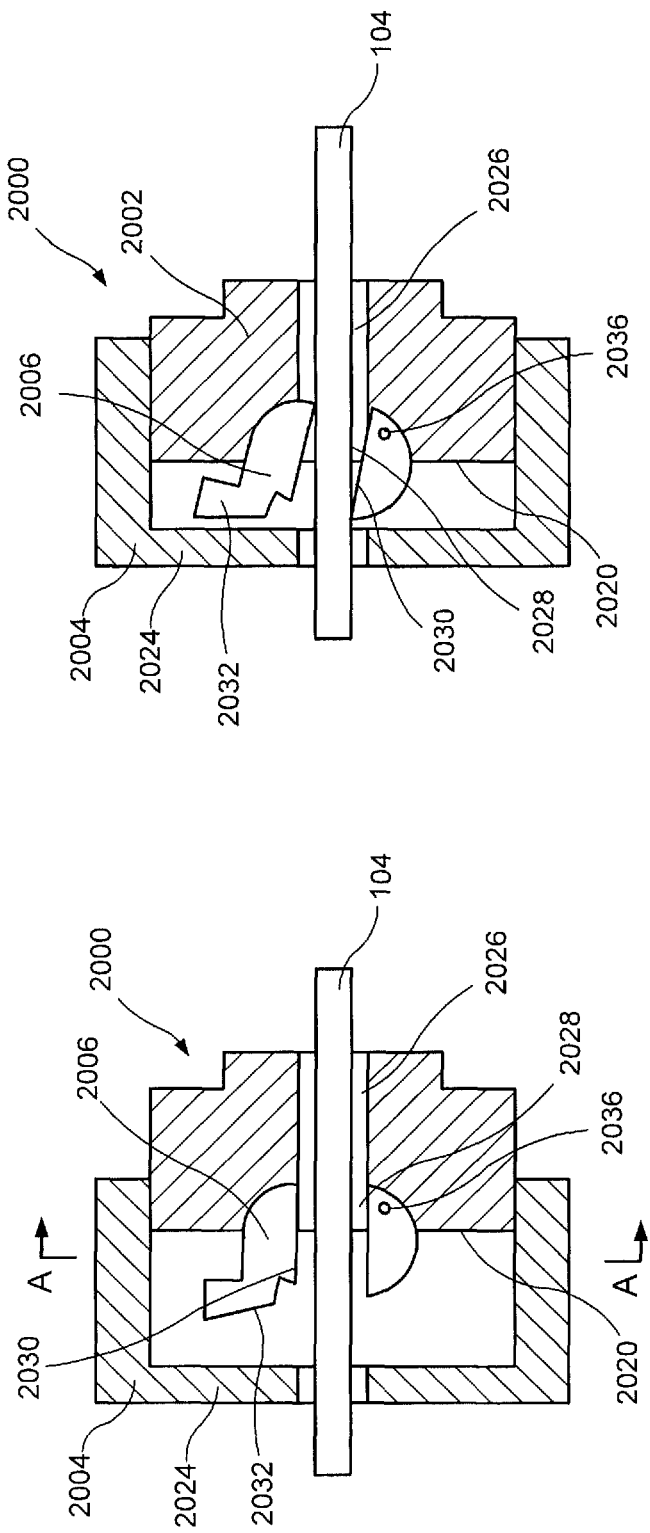

INTERNAL CABLE FIXATOR

PRIORITY CLAIM

The present invention claims priority to U.S. Provisional Application Ser. No. 61/186,141 entitled "Internal Cable Fixator" filed on Jun. 11, 2009, the entire disclosure of which is incorporated herein by reference.

FIELD OF THE INVENTION

The present application relates to a system and method for treating fractures and, in particular, relates to internal fixation devices for treating fractures.

BACKGROUND

Acetabular (hip socket) fractures are serious orthopedic injuries usually resulting from significant trauma. Surgery to realign and stabilize the displaced joint surfaces (e.g., using plates and screws), allows the patient to avoid traction and prolonged bedrest. Accurate fracture realignment promotes improved bone and cartilage healing, which in turn improves long-term results. Early fracture stability allows comfortable hip movement which improves joint cartilage healing. Additionally, this allows patients to be out of bed and ambulatory.

However, acetabular fractures with medial displacement patterns, particularly those with medial displacement of the quadrilateral surface, may be technically challenging to treat. The location of the affected area deep in the pelvic part of the abdominal cavity, minimal bone stock and difficulty obtaining stable internal fixation in the true pelvis contribute to the surgical challenge of open reduction and internal fixation of such fractures. Applying a medial buttress plate across the quadrilateral surface may assist in preventing the femur head from penetrating into the pelvic cavity. However, because of the limited access to the quadrilateral surface and the thin bone structures around the acetabulum, it is often difficult to treat such fractures with standard plates and screws. Although procedures have previously been described for treating quadrilateral surface fractures, there is still no optimal mechanical solution. Most of the techniques involve fixations with forces acting at 90° to a screw axis, which may, when bone thickness is limited, result in a cut out of the screws.

SUMMARY OF THE INVENTION

The present invention is directed to a cable fixation device, comprising a clamp including a head portion and a body portion along with a lumen extending therethrough, the head portion removably coupleable with an actuating mechanism, the lumen sized and shaped to slidably accommodate a cable in combination with a clamping ring including a channel extending therethrough, the channel including a first portion and a second portion, the first portion being sized and shaped to slidably accommodate the cable therethrough, the second portion being sized and shaped to engage the clamp, wherein a portion of the clamp is movable between a first configuration and a second configuration, the cable slidable therethrough in the first configuration, the portion of the clamp moving radially inward in the second configuration to clamp the cable.

BRIEF DESCRIPTION OF THE DRAWINGS

FIG. 2 shows an exploded perspective view of a cable fixation device of the system of FIG. 1;

FIG. 3 shows a perspective view of the cable fixation device of FIG. 2;

FIG. 9A shows a perspective view of a plate of the system of FIG. 1;

FIG. 9B shows a perspective view of the plate of FIG. 9A with a cable inserted therethrough;

FIG. 16 shows an exploded perspective view of the cable fixation device according to a fourth exemplary embodiment of the present invention;

FIG. 17 shows a cross-sectional side view of the cable fixation device of FIG. 16;

FIG. 24 shows an exploded perspective view of a cable fixation device according to an eighth exemplary embodiment of the present invention;

FIG. 25 shows a cross-sectional side view of the cable fixation device of FIG. 24;

FIG. 26 shows an exploded perspective view of a cable fixation device according to a ninth exemplary embodiment of the present invention;

FIG. 27 shows a cross-sectional side view of the cable fixation device of FIG. 26;

FIG. 30 shows a side view of a cable fixation device according to an eleventh exemplary embodiment of the present invention, in a first configuration;

FIG. 31 shows a side view of the cable fixation device of FIG. 30, in a second configuration; and FIG. 32 shows a side view of a cable fixation device according to a twelfth exemplary embodiment of the present invention, in a first configuration.

FIG. 33 shows a side view of the cable fixation device of FIG. 32, in a second configuration;

FIG. 36 shows a cross-sectional side view of a cable fixation device according to a thirteenth exemplary embodiment of the present invention, in a first method of use;

FIG. 37 shows a cross-sectional side view of the cable fixation device of FIG. 36 according to a second method of use;

FIG. 38 shows a perspective view of an alternate embodiment of the cable fixation device of FIG. 36;

FIG. 39 shows a cross-sectional side view of the cable fixation device of FIG. 38, according to a first method of use;

FIG. 40 shows a cross-sectional side view of the cable fixation device of FIG. 38, according to a second method of use;

FIG. 43 shows a cross-sectional side view of a cable fixation device according to a fifteenth exemplary embodiment of the present invention;

FIG. 44 shows a cross-sectional side view of an alternate embodiment of the cable fixation device of FIG. 43;

FIG. 51 shows a cross-sectional side view of a cable fixation device according to a nineteenth exemplary embodiment of the present invention, in a first configuration;

FIG. 52 shows a cross-sectional side view of the cable fixation device of FIG. 51, in a second configuration;

FIG. 55 shows a cross-sectional side view of a cable fixation device according to a twentieth exemplary embodiment of the present invention, in a first configuration;

FIG. 56 shows a cross-sectional side view of the cable fixation device of FIG. 55, in a second configuration;

FIG. 57 shows a cross-sectional view of the cable fixation device of FIG. 55, along line A-A;

DETAILED DESCRIPTION

The present invention, which may be further understood with reference to the following description and the appended drawings, relates to a system and method for treating fractures, and in particular relates to internal fixation devices for treating fractures. Specifically, exemplary embodiments of the present invention describe a system and method for securing a cable or wire through the fractured quadrilateral surface of the acetabulum. It should be noted however, that although the embodiments of the present invention are described in regard to the application of a buttress plate to the quadrilateral surface of the acetabulum using surgical cable or wire, the present invention is relevant to the use of cable or wire to secure any bone fixation device to any bone.

Figure 1:
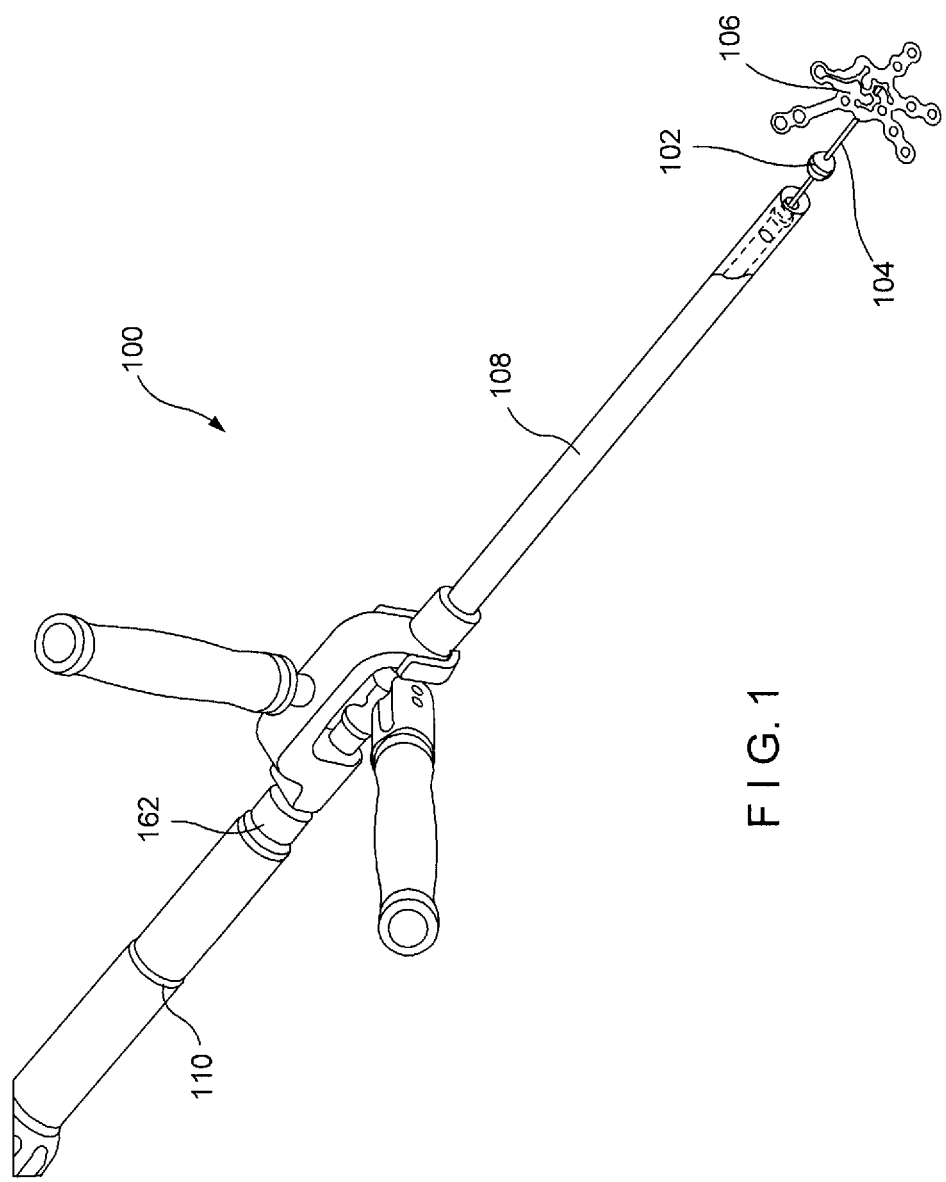
FIG. 1 shows a perspective view of a system according to a first exemplary embodiment of the present invention.
Figure 4:
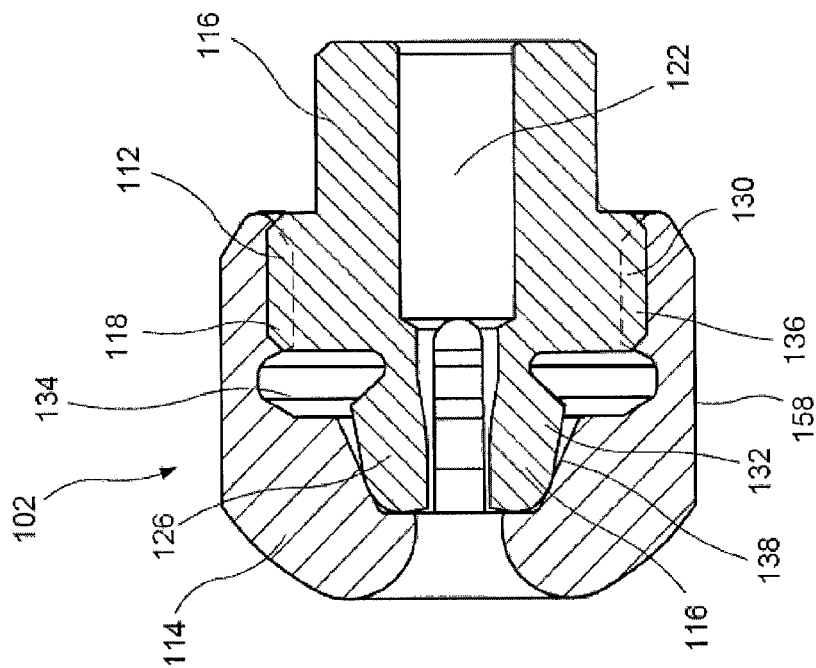
FIG. 4 shows a partially cross-sectional side view of the cable fixation device of FIG. 2, in a first configuration.
Figure 5:
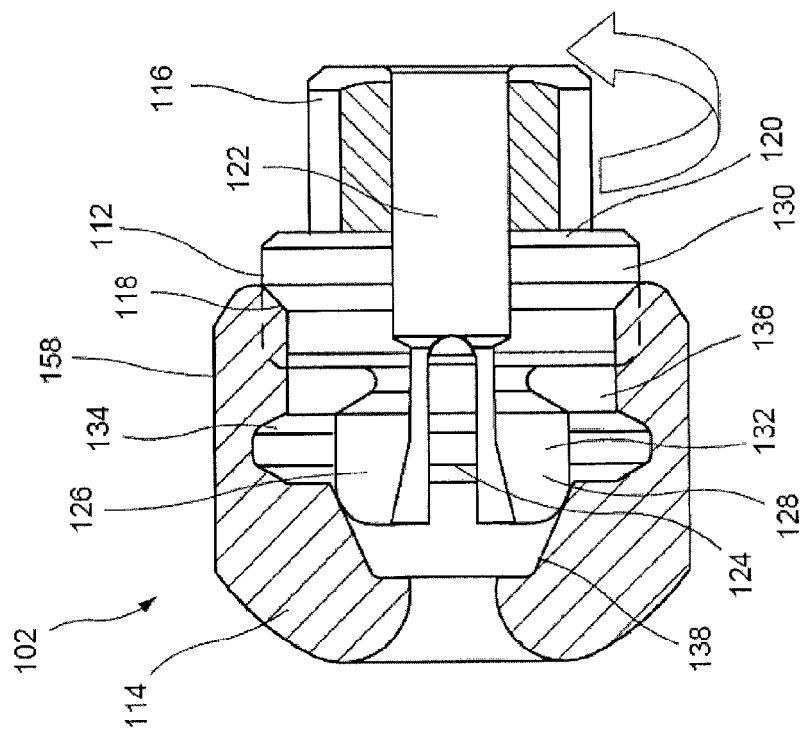
FIG. 5 shows a cross-sectional side view of the cable fixation device of FIG. 2, in a second configuration.

As shown in FIG. 1, a system 100 according to an exemplary embodiment of the present invention comprises a wire or cable fixation device 102, which may be clamped over a wire or cable 104 at a desired location and tension as will be described in more detail below. The cable fixation device 102 may be used to fix a plate 106, such as a buttress plate, to a surface of a bone, such as a quadrilateral surface. The system 100 may further comprise a clamping tool 108 for clamping the cable fixation device 102 and a tensioner 110 for applying tension to the cable 104. As will be described in more detail below, the cable 104 is inserted through and coupled to the plate 106, passed through the bone and fed through the cable fixation device 102. The clamping tool 108 may mate with a portion of the cable fixation device 102 to secure the cable fixation device 102 over the cable 104.

As shown in FIGS. 2-5, the cable fixation device 102 may further comprise a clamp 112, which accommodates the cable 104 and a clamping ring 114, which accommodates a portion of the clamp 112 to fix the cable 104 therewithin. The clamp 112 includes a lumen 122 extending through an entire length thereof along with a head 116 and a body 118 extending distally of a distal end 120 of the head 116. The lumen 122 is sized and shaped to slidably accommodate the cable 104. The head 116 sized and shaped to engage a portion of the clamping tool 108 such that the clamp 112 may be rotated about a longitudinal axis of the system 100, relative to the clamping ring 114. For example, in a preferred embodiment, the head 116 may be hexagonally shaped to be non-rotatably received in a correspondingly shaped distal end of the clamping tool 108.

The body 118 includes a first portion 130 and a second portion 132. The first portion 130 extends distally from the distal end 120 of the head 112, while the second portion 132 extends distally of the first portion 130. A longitudinal slot 124 extends through at least a portion of a length of the body 118, preferably through a length of the second portion 132, thereby forming first and second jaws 126, 128, respectively, which are movable relative to one another to clamp the cable 104 therebetween. The longitudinal slot 124 may be substantially parallel to or along the longitudinal axis of the system 100. Although the clamp 112 is described as including a single longitudinal slot 124 to form two jaws 126, 128, it will be understood by those of skill in the art that the clamp 112 may include any number of longitudinal slots 124 to form any number jaws so long as the jaws are moved radially inward to clamp the cable 104 therebetween. The first portion 130 may include threading (not shown) for engaging the clamping ring 114.

The clamping ring 114 includes a lumen 134 extending therethrough. The lumen 134 includes at least a first portion 136 sized and shaped to accommodate the first portion 130 of the body and a second portion 138 sized and shaped to accommodate the second portion 132 of the body 118. The first portion 136 may engage the first portion 130 of the body 118. In a preferred embodiment, the first portion 136 is substantially circular and includes a threading (not shown) for engaging the first portion 130 of the body 118. The second portion 138 may be smaller in diameter than the first portion 136 and smaller than the second portion 132 of the clamp 112 such that insertion of the clamp 112 into the lumen 134 of the clamping ring causes the jaws 126, 128 of the clamp 112 to move toward one another as an outer surface 140 of the second portion 132 engages the second portion 138, clamping the cable 104 between the jaws 126, 128. Thus, in an operative position, the clamping ring 114 is positioned distally of the clamp 112 such that the clamp 112 may be rotated relative to the clamping ring 114 to fix the clamping device 102 at a desired position and tension along the cable 104. In a preferred embodiment, an outer surface 158 of the clamping ring 114 may be hexagonally shaped to be non-rotatably received in a correspondingly shaped distal end of the clamping tool 108.

Figure 6:
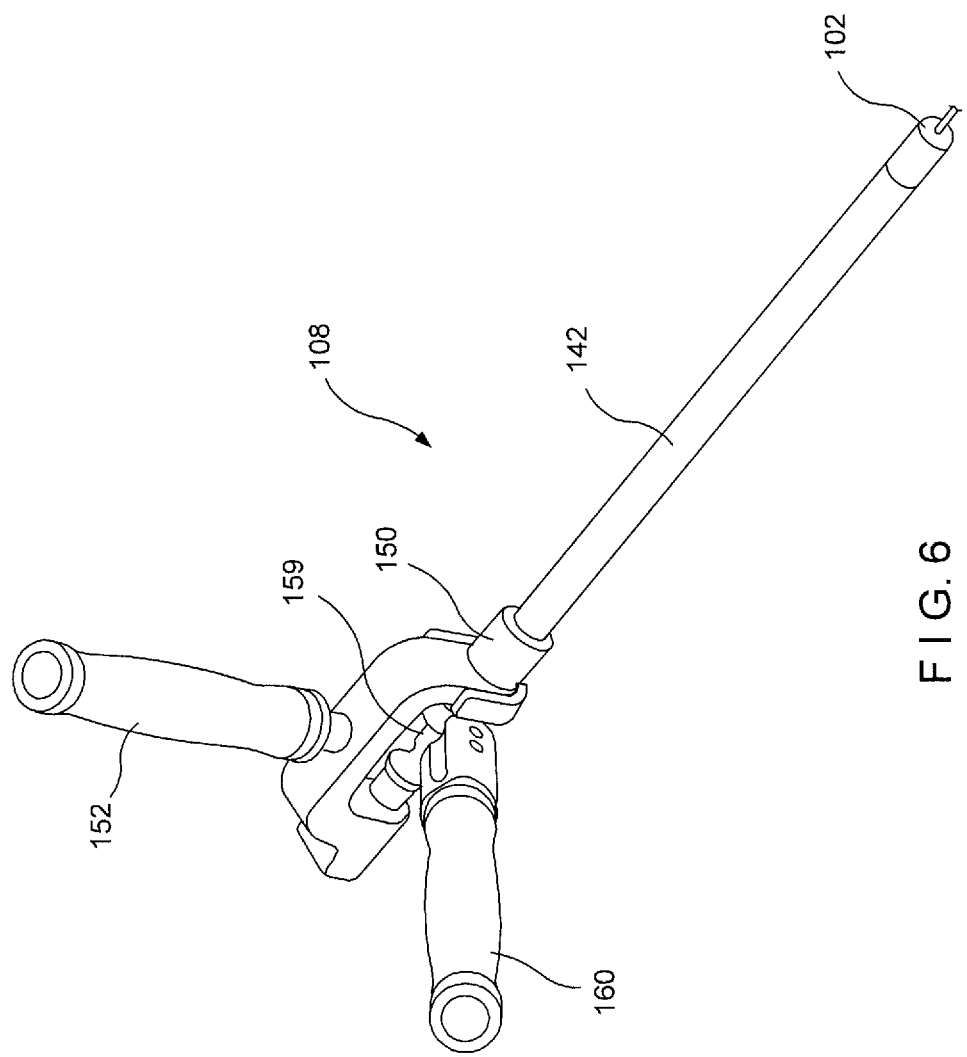
FIG. 6 shows a perspective view of a clamping tool of the system of FIG. 1.
Figure 7:
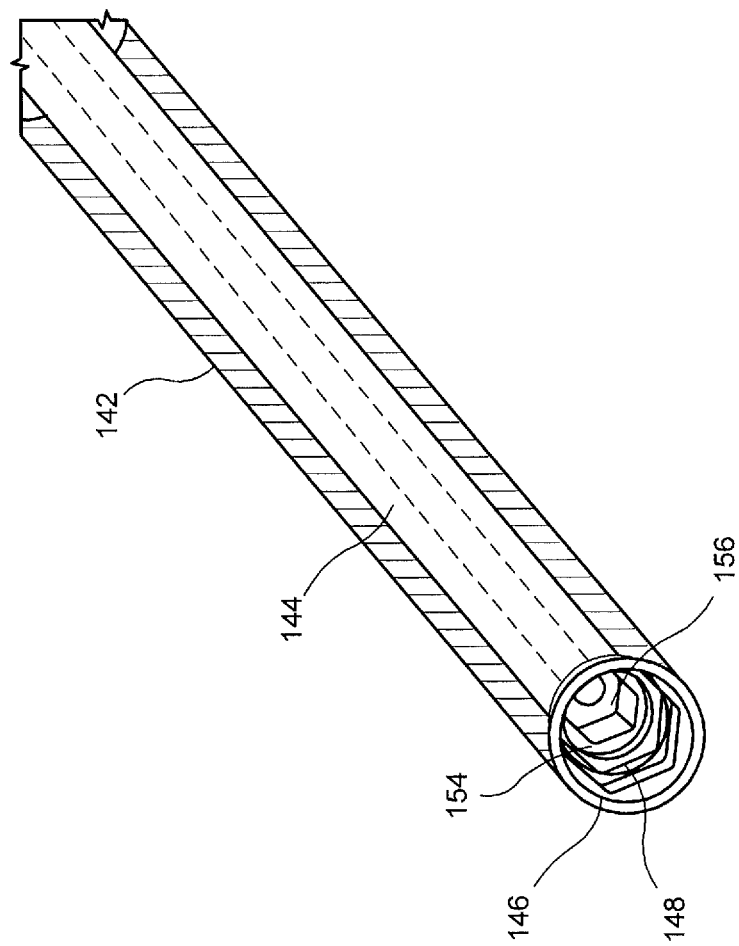
FIG. 7 shows an enlarged perspective view of a distal end of the clamping tool of FIG. 6.

As shown in FIGS. 6-7, the clamping tool 108 may be substantially longitudinal, including an outer sleeve 142 and an inner sleeve 144 rotatably housed therewithin. A distal end 146 of the outer sleeve 142 includes a recess 148 shaped to engage the outer surface 158 of the clamping ring 114 to prevent the clamping ring 114 from rotating relative thereto. In a preferred embodiment, for example, the recess 148 may be hexagonally shaped to accommodate a hexagonally shaped clamping ring 114. However, it will be understood by those of skill in the art that a variety of shapes may be selected for the clamping ring 114 and the recess 148 so long as the two elements are non-rotatably coupleable to one another. A proximal end 150 of the outer sleeve 142 may include a handle 152 that may be held by a surgeon or other user to prevent rotation of the outer sleeve 142 relative to the longitudinal axis of the system 100. The proximal end 150 of the outer sleeve 142 may also include a mating feature for non-rotatably engaging with a distal end 162 of the tensioner 110.

A distal end 154 of the inner sleeve 144 includes a mating feature sized and shaped to non-rotatably engage the head 116 of the clamp 112 such that rotating of the inner sleeve 144 relative to the outer sleeve 142 rotates the clamp 112 relative to the clamping ring 114, screwing the body 118 of the clamp 112 into the clamping ring 114. In a preferred embodiment, the mating feature of the distal end 154 may include a recess 156 for engaging the hexagonally shaped head 116 of the clamp 112. It will be understood by those of skill in the art, however, that a variety of shapes may be selected for the recess 156 and the head 116 so long as the distal end 154 of the inner sleeve 144 and the head 116 of the clamp 112 are non-rotatably coupleable to one another to prevent rotation thereto. A proximal end 159 of the inner sleeve 144 may be hexagonally shaped to be able to connect to a handle with wrench 160 that may be used to rotate the inner sleeve 144 relative to the outer sleeve 142.

Figure 8:
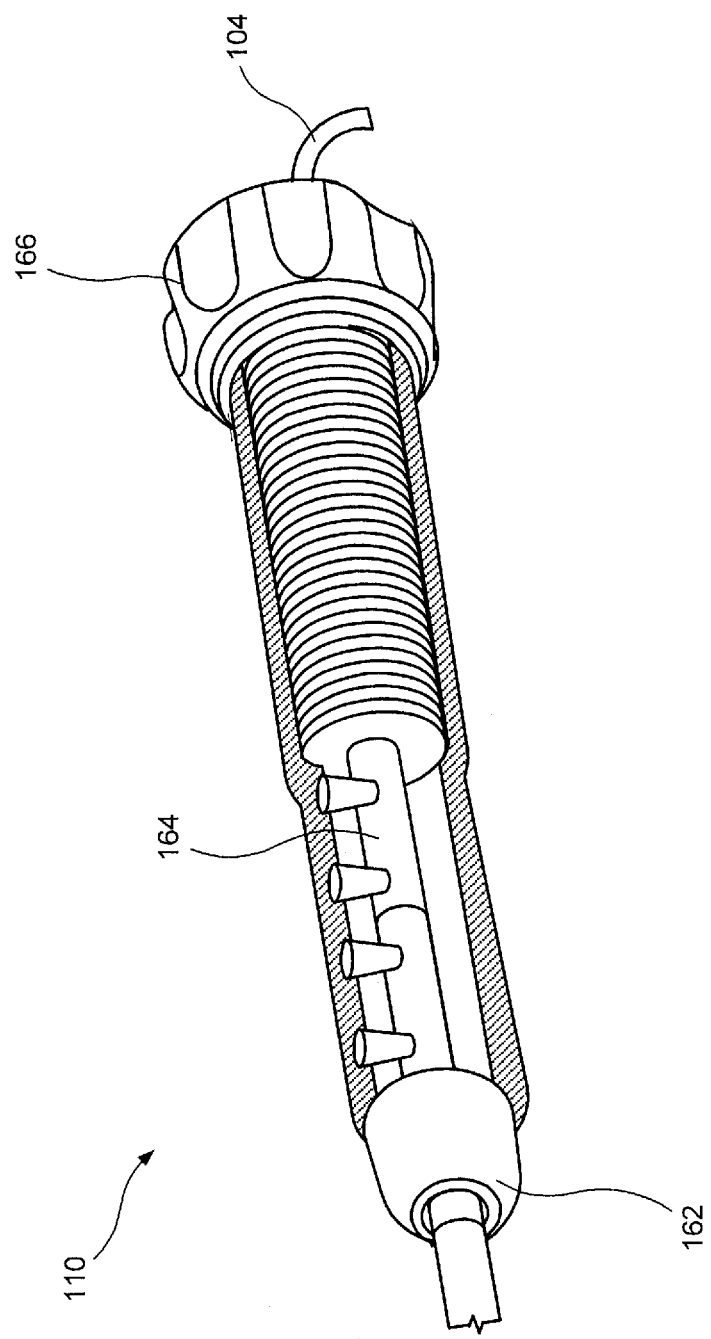
FIG. 8 shows a perspective view of a tensioner of the system of FIG. 1.

As shown in FIG. 8, the tensioner 110 may also be substantially longitudinal, including a channel 164 extending therethrough for slidably accommodating the cable 104. However, it will be understood by those of skill in the art that the shape of the handle is not critical to the invention and may be any selected shape. The distal end 162 of the tensioner 110 may be matable with the clamping tool 108 such that the channel 164 is substantially aligned with the inner sleeve 144. In an exemplary embodiment, the distal end 162 may includes a recess adapted to receive a complimentarily shaped proximal end of the outer sleeve 142 of the clamping tool 108 to prevent rotation of the outer sleeve 142 relative to the tensioner 110. Thus, the cable 104 may extend through a length of the cable fixation device 102, through the inner sleeve 144 of the clamping tool 108 and through the channel 164 of the tensioner 110. The channel 164 extends to a tensioning mechanism operated by a knob 166 formed, for example, at a proximal end of the tensioner 110. As would be understood by those of skill in the art, the tensioning mechanism may, for example, include a spindle coupled to the knob 166. The cable 104 is coupled to the spindle and a ratchet mechanism, or other suitable device maintains tension on the cable 104 as the cable 104 is wound up on the spool by the rotation of the knob 166. As would be understood by those of skill in the art, the tensioning mechanism may further include a manual release disengaging the ratchet mechanism to release tension from the cable 104 as desired. The tensioner 110 may further include an indicator or scale allowing a user to determine a current level of tension on the cable 104.

A method according to an exemplary method of the present invention comprises clamping the cable fixation device 102 in a desired position along the cable 104 such that a fracture of the bone may be fixed using, for example, the plate 106. The plate 106 may be selected according to the type of fracture of the bone and the support required to reduce the fracture. For example, for fixing a fracture in the quadrilateral surface of the acetabulum, the plate 106, as shown in FIG. 9A, may include one or more buttressing wings 168 and a brim fixation wing 170. The buttressing wings 168 may be pre-bent to adapt to the curve and shape of the quadrilateral surface. Additionally, the brim fixation wing 170 may be pre-bent to fit the pelvic brim. Alternatively, a user of the plate 106 may shape the plate 106 as desired to accommodate the anatomy of the target area as would be understood by those skilled in the art. Thus, the plate 106 is preferably formed of a material sufficiently strong to withstand the forces to which it will be exposed when implanted, but which is also sufficiently flexible to adapt to the shape of the bone and to receive any bending required by a user. The plate 106 may be assembled with the cable 104 inserted through a hole 172 formed, for example, at or near a center thereof so that tension applied to the cable 104 draws the entire plate 106 snugly against the bone. It will be understood by those of skill in the art that the plate 106 may include any number of holes 172 adapted and configured to accommodate the cable 104. The cable 104 may be fixed to the plate 106 by any known mechanism (e.g., by an enlarged distal end sized to prevent the cable 104 from slipping through the plate 106 and in combination with a washer). The plate 106 may include additional opening 174 for accommodating other fixation elements.

The plate 106 may be positioned over a surface of the bone and the cable 104 inserted through the hole 172 in the plate 106 and a hole in the bone, which may be drilled in an appropriate position. A proximal end of the cable 104 may be inserted through the plate 106 and the bone until a distal end of the cable 104 abuts the plate 106. The distal end of the cable 104 may be enlarged to prevent the distal end from passing through the plate 106. A remaining portion of the cable 104 may be inserted through the cable fixation device 102, the inner sleeve 144 of the clamping tool 108 and the channel 168 of the tensioner 110. The cable fixation device 102 may be slid along the cable 104 until the clamping ring 114 abuts the bone. The clamping tool 108 is engaged to the cable fixation device 102 and the tensioner 110 engaged to the clamping tool 108, as described above. The knob 166 of the tensioner 110 may be turned such to add a desired tension to the cable 104. Once the desired amount of tension is placed on the cable 104, the inner sleeve 144 of the clamping tool 108 may be rotated relative to the outer sleeve 142, rotating the clamp 112 relative to the clamping ring 114 such that the clamp 112 engages the clamping ring 114 and the cable 104 is engaged therewithin.

Alternatively, the plate 106 may include an opening 176 connected to a channel 178 extending through a central portion 180 of the plate 106 in a pattern. The opening 176 may be sized and shaped to permit the enlarged distal end of the cable 104 to be inserted therethrough, while a width of the channel 178 is sized and shaped to prevent the enlarged distal end of the cable 104 from passing therethrough. Thus, the plate 106 may be positioned over the bone, as desired, and the enlarged distal end of the cable 104 may be inserted through the opening 176. The cable 104 may then be slid through the channel 178 to a desired position along the channel 178 to fix the plate 106, as shown in FIG. 9B.

As shown in FIGS. 10-13, a cable fixation device 200 according to a second exemplary embodiment of the present invention comprises a clamp 202 and a clamping ring 204 (e.g., an adaptation ring) engagable with one another in an operative position. As would be understood by those skilled in the art, the clamp 202 is formed as an eccentric body so that rotation of the clamp 202 moves a lumen 210 thereof out of alignment with the a first portion 218 of a channel 216 of the clamping ring 204 as will be described in more detail below. The cable fixation device 200 may be used in the system 100, in substantially the same manner as the cable fixation device 102. The clamp 202 includes a head 206, a body 208 and a lumen 210 extending therethrough. The head 206 is preferably sized and shaped to be engaged by the inner sleeve 144 of the clamping tool 108 as described above in regard to the system 100. In one embodiment, the head 206 may be hexagonally shaped to engage the distal end 154 of the inner sleeve 144, which may be a correspondingly shaped hexagonal recess. The body 208 may be substantially cylindrical, including a threading or other mating component 212 on an outer surface 214 thereof to prevent disengaging of the clamp 202 and the clamping ring 204 and to provide a tactile indication to a user when the clamp 202 and the clamping ring have been fully moved to the locked position. The lumen 210 extends through the head 206 and the body 208, but is off-center such that the lumen 210 is parallel to a longitudinal axis of the clamp 202 rather than co-axial with the longitudinal axis.

A channel 216 extending through the clamping ring 204 includes a first portion 218 sized and shaped to slidably accommodate the cable 104 and a second portion 220 proximal of the first portion 218 sized and shaped to accommodate the body 208 of the clamp 202. The second portion 220 may include a corresponding mating component 222 for mating with the clamp 208. An outer surface 224 of the clamping ring 204 may be shaped to accommodate the distal end 146 of the outer sleeve 142 such that the clamp 202 may be rotated relative to the clamping ring 204 about a longitudinal axis of the device 200 via the clamping tool 108. In a preferred embodiment, the outer surface 224 may be hexagonally shaped to accommodate a hexagonally shaped recess in the distal end 146 of the outer sleeve 142. Once the clamp 202 has engaged the inner sleeve 144 of the clamping tool 108 and the clamping ring 204 has engaged the outer sleeve 142, the clamp 202 and the clamping ring 204 may be rotated relative to one another.

Figure 11:
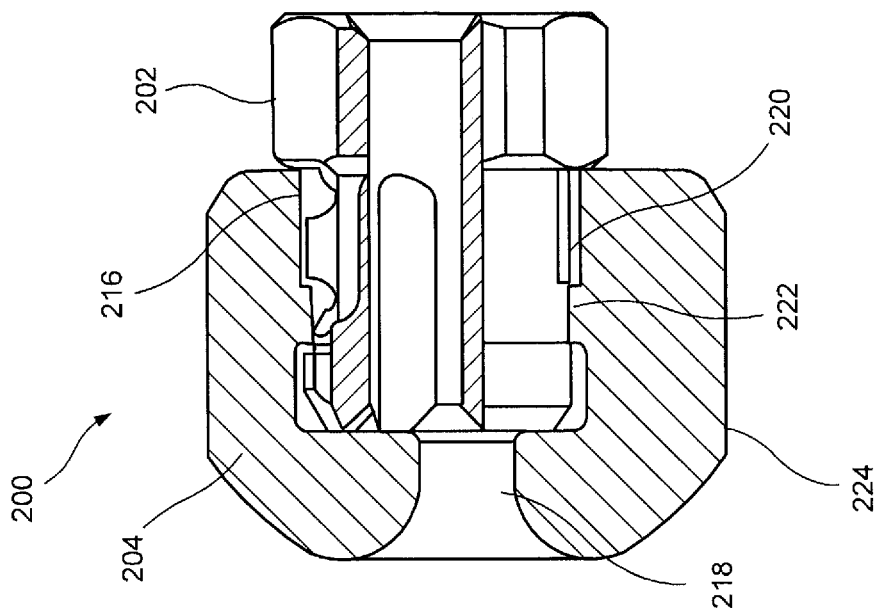
FIG. 11 shows a cross-sectional side view of the cable fixation device of FIG. 10.
Figure 10:
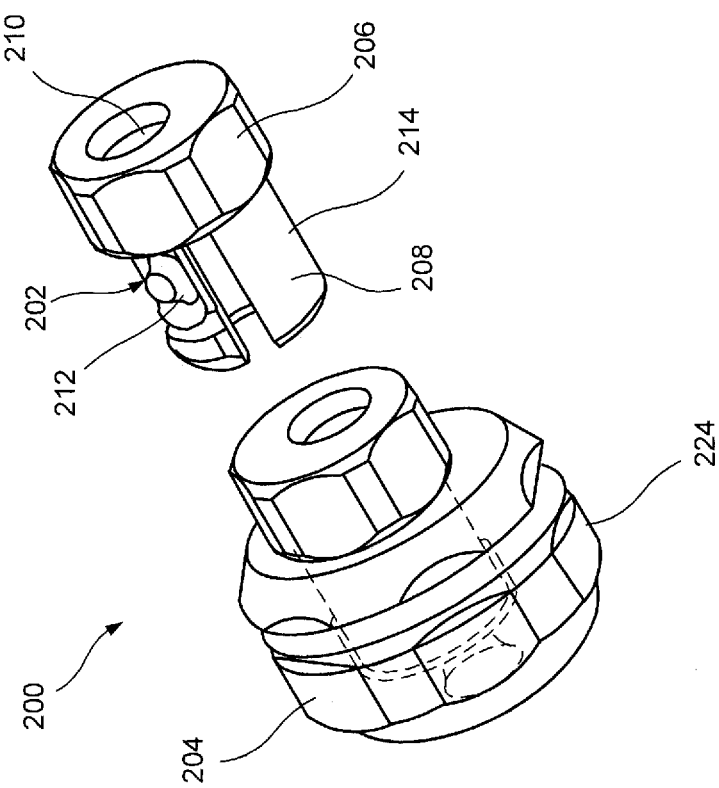
FIG. 10 shows an exploded perspective view of a cable fixation device according to a second exemplary embodiment of the present invention.
Figure 13:
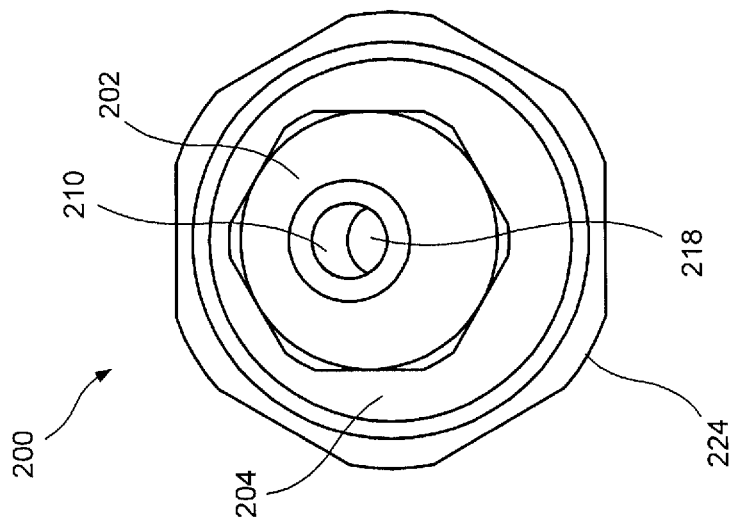
FIG. 13 shows a bottom view of the cable fixation device of FIG. 10, in a second configuration.
Figure 12:
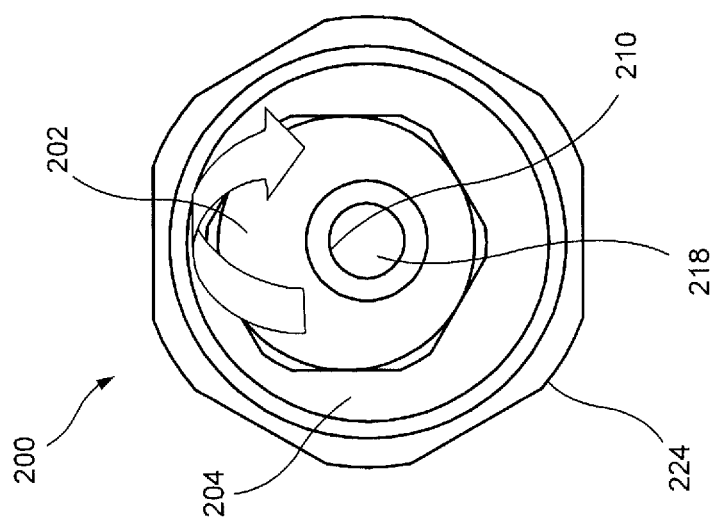
FIG. 12 shows a bottom view of the cable fixation device of FIG. 10, in a first configuration.

In a first configuration, the lumen 210 is substantially aligned with the first portion 218 such that the device 200 may be slid over the cable 104 in the first configuration. Once the cable 104 has been tensioned to the desired tension and the device 200 has been positioned in a desired location along the cable 104, the clamp 202 may be rotated relative to the clamping ring 204 about the longitudinal axis of the device 200 via rotation of the inner sleeve 144 relative to the outer sleeve 142 such that the device 200 is moved to a second configuration, as shown in FIGS. 11 and 13. In the second configuration, the lumen 210 of the clamp 202 is offset from the first portion 218 of the channel 216 of the clamping ring 204, pressing against the cable 204 passing therethrough such that the cable 104 is fixed therein. In a preferred embodiment, the clamp 202 may be rotated relative to the clamping ring 204 180 degrees from the first configuration to the second configuration, moving the lumen 210 from a position in which it is aligned with the first portion 218 to a position in which it is offset from the first portion 218, to grip the cable 104 passing therethrough.

Figure 15:
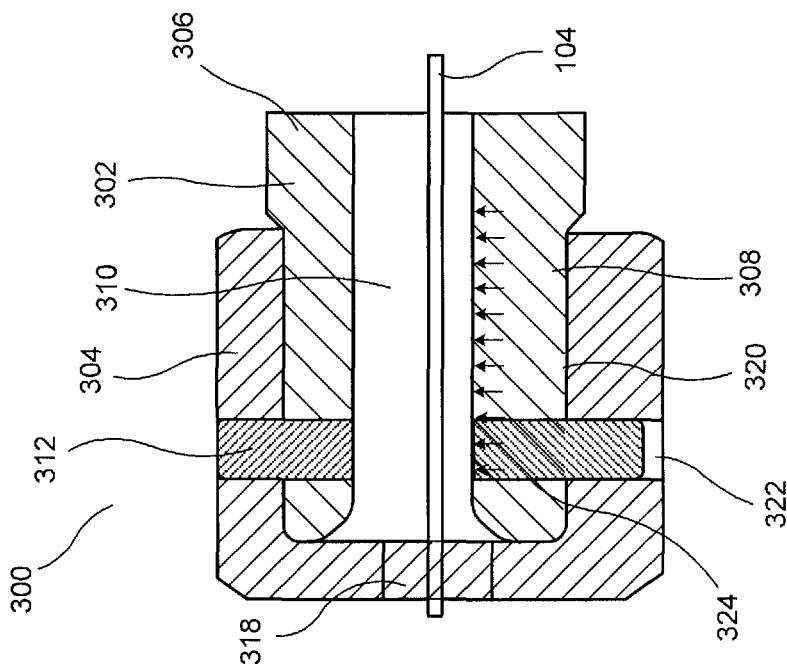
FIG. 15 shows a cross-sectional side view of the cable fixation device of FIG. 14.
Figure 14:
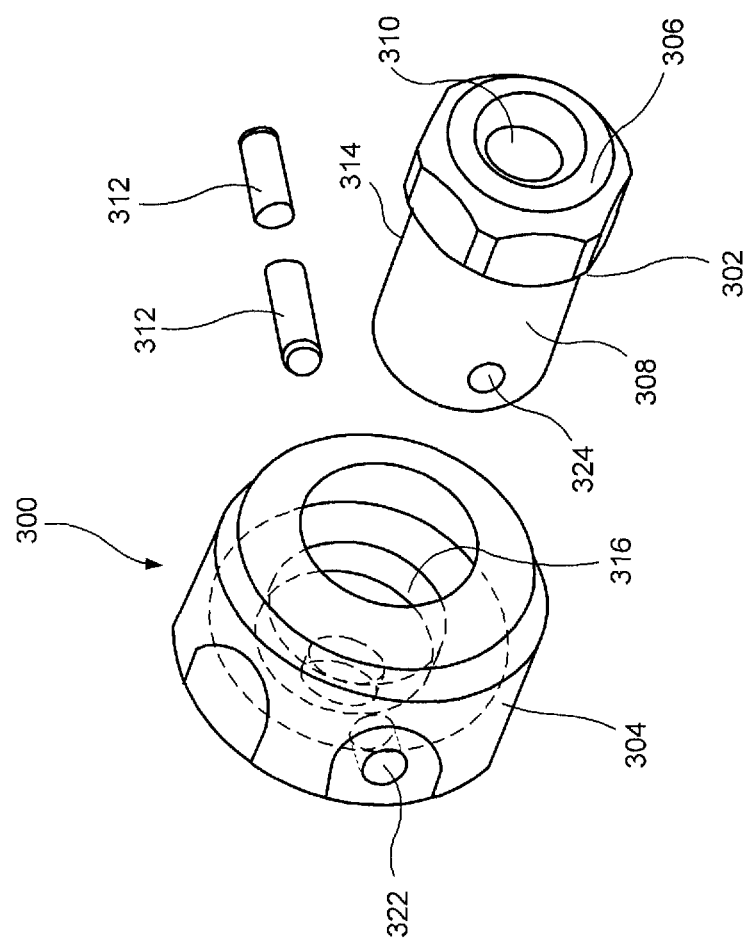
FIG. 14 shows an exploded perspective view of a cable fixation device according to a third exemplary embodiment of the present invention.

As shown in FIGS. 14-15, a cable fixation device 300 according to a third exemplary embodiment of the present invention comprises a clamp 302 and a clamping ring 304. The cable fixation device 300 further comprises an insert 312 for fixing the clamp 302 relative to the clamping ring 304. The clamping device 300 may be used in the system 100 as described above, in place of the clamping device 102. The clamp 302 and the clamping ring 304 are movable relative to one another from a first configuration in which the cable 104 is slidable therethrough to a second configuration in which the cable 104 is fixed therein. The clamp 302 and the clamping ring 304 are substantially similar to the device 200, described above. The clamp 302 includes a head 306, body 308 and a lumen 310 extending therethrough such. The head 306 may be sized and shaped to mate with the distal end 154 of the inner sleeve 144 of the clamping tool 108.

Similarly to the clamping ring 204, a channel 316 extending through the clamping ring 304 includes a first portion 318 slidably accommodating the cable 104 and a second portion 320 for accommodating the body 308. In the first configuration, the lumen 310 of the clamp 302 is substantially aligned with the first portion 318 of the channel 316, but when rotated relative to the clamping ring 304 to the second configuration, the lumen 310 is offset from the first portion 318.

Similarly to the device 200, the clamp 302 may be rotated 180° relative to the clamping ring 304 such that the body 308 of the clamp 302 is engaged with the second portion 320 of the channel 316 of the clamping ring 304, moving from the first configuration to the second configuration. In the first configuration, the lumen 310 of the clamp 302 is substantially coaxial with the first portion 318 of the clamping ring 304. When in the second configuration, however, the clamp 302 is rotated such that the lumen 310 axially offset from the first portion 320, parallel to an axis of the first portion 318 such that the cable 104 passing through the lumen 310 and the channel 316 is clamped therebetween. Rather than engaging with a threading or other mating mechanism however, the body 308 of the clamp 302 and the clamping ring 304 engage one another via insertion of the insert 312 into an opening 322 in the clamping ring 304 and a corresponding opening 324 in the body 308 of the clamp 302. Thus, it will be understood by those of skill in the art that once the cable fixation device 300 is moved into the second configuration, the insert 312 may be used to fix the clamp 302 relative to the clamping ring 304, maintaining the device 300 in the second configuration.

As shown in FIGS. 16-17, a cable fixation device 400 according to a fourth exemplary embodiment of the present invention, which may be used in the system 100 described above, comprises a clamp 402, a clamping ring 404 and a damper 406 movable between a first configuration and a second configuration to clamp a cable therein in a manner similar to that described above. The clamp 402 includes a head 408, a body 410 and a lumen 412 extending therethrough. The head 408 includes a distal surface 414 and a proximal surface 416. The distal surface 414 may be shaped and or configured to abut either the plate 106 or a bone that is being fixed. The proximal surface 416 may be shaped and/or configured to abut a distal end 418 of the clamping ring 404. It will be understood by those of skill in the art, however, that the clamping ring 404 is not required to abut the proximal surface 416 of the clamp 402 and may instead come into close contact with one another. The head 408 may be shaped to engage the distal end of 146 of the outer sleeve 142 of the clamping tool 108

The lumen 412 is sized and shaped to slidably accommodate the cable 104 therethrough. The body 410 includes a recessed portion 420 proximal of the head 408 that is sized and shaped to accommodate the damper 406 and includes an opening 422 into the lumen 412. The recessed portion 420 may have a diameter that is smaller than a diameter of a remaining portion 424 of the body 410. The remaining portion 424 may include a threading (not shown) or other arrangement for engaging with a portion of the clamping ring 404.

The damper 406 may be slidable over the recessed portion 420 and movable between the first configuration and the second configuration. In the first configuration, the damper 406 is positioned over the recessed portion 420 but does not extend into the opening 422 of the recessed portion 420 such that a cable may slidably pass through the lumen 412 in the first configuration. In the second configuration, the damper 406 moves relative to the clamp 402 into the opening 422 of the recessed portion 420, decreasing a cross-section of the lumen 412 gripping the portion of the cable 104 passing therethrough against the damper 406 and fixing the cable 104 in position relative to the clamp 402. The damper 406 may further included an angled surface 432 at a proximal end 434 thereof for contacting a portion of the clamping nut 404 such that movement of the clamping nut 404 relative to the clamp 402 moves the damper 406 from the first configuration to the second configuration.

A channel 426 extending through the clamping ring 404 for engaging the clamp 402 includes a first portion 428 and a second portion 430. The first portion 428 is sized and shaped to accommodate the damper 406 and the recessed portion 420 of the body 410 of the clamp 402 when in the first configuration. The second portion 430 is sized and shaped to accommodate the remaining portion 424 of the body 410. The second portion 430 may include a threading (not shown) or other arrangement for engaging the clamping ring 404 with the clamp 402. A diameter of the first portion 428 may be larger than a diameter of the second portion 430 since the first portion 428 must also accommodate the damper 406. A shoulder 436 including an angled surface 438 formed between the first portion 428 and the second portion 430 contacts the angled surface 432 of the damper 406 as the damper 406 is moved from the first configuration to the second configuration. That is, as the clamping ring 404 is moved toward the clamp 402 (i.e., to the second configuration), the angled surface 438 of the clamping ring 404 is forced over the angled surface 432 of the damper 406, forcing the damper 406 radially inward into the opening 422 fixing the cable 104 extending therethrough relative to the clamp 402.

Thus, as the clamping ring 404 is moved relative to the clamp 402 by, for example, rotating the clamping ring 404, the clamping ring 404 moves over the body 410 of the clamp 402 such that the clamping ring 404 and the clamp engage one another. Where the clamp 402 and the clamping ring 404 include threading, the threading of each of the clamp 402 and the clamping ring 404 engage one another to fix the clamp 402 to the clamping ring. An outer surface 440 of the clamping ring 404 may be shaped to accommodate the distal end 154 of the inner sleeve 144 of the clamping tool 108 such that as the inner sleeve 144 and the outer sleeve 142 are rotated relative to one another, the clamping ring 404 and the clamp 402 rotate relative to one another.

Figure 19:
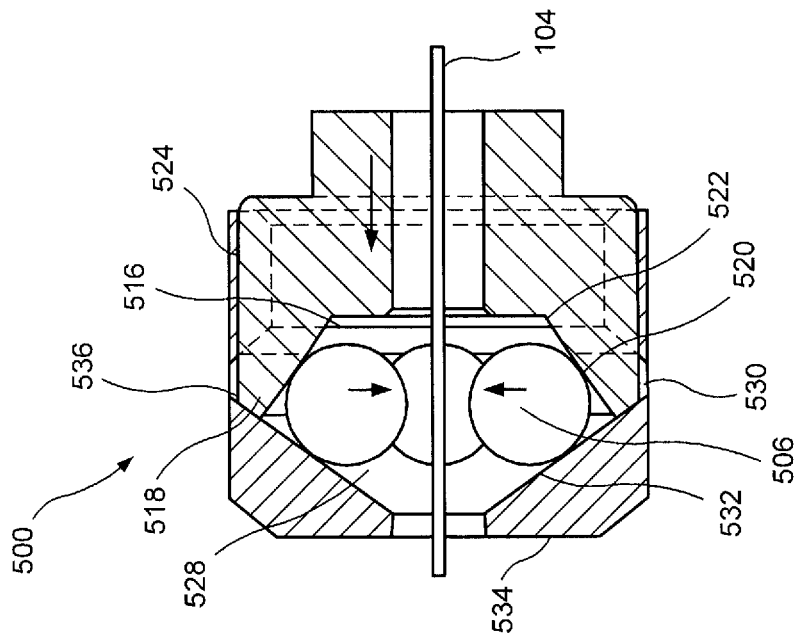
FIG. 19 shows a cross-sectional side view of the cable fixation device of FIG. 18.
Figure 18:
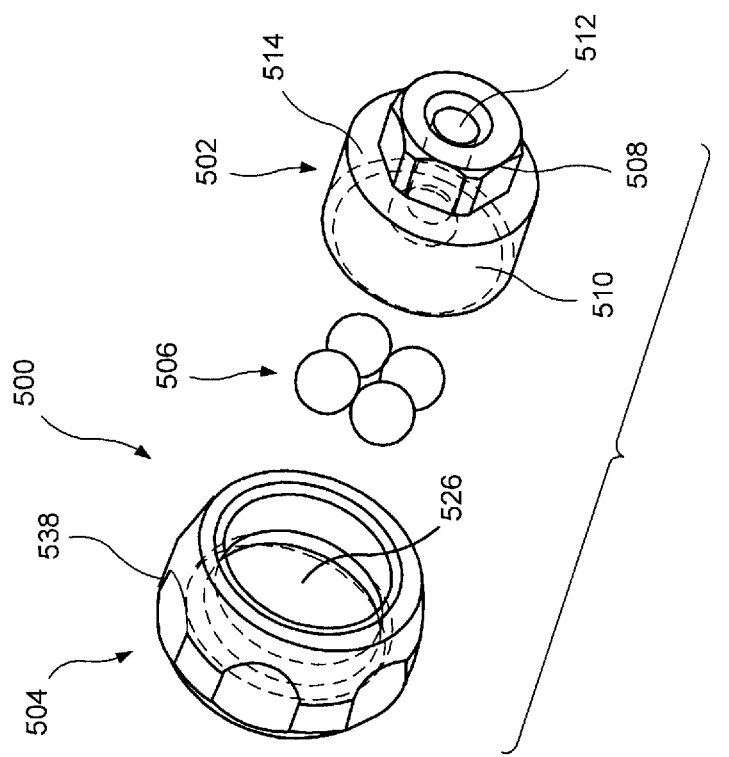
FIG. 18 shows an exploded perspective view of a cable fixation device according to a fifth exemplary embodiment of the present invention.

As shown in FIGS. 18-19, a cable fixation device 500 according to a fifth exemplary embodiment of the present invention, which may be used in place of the cable fixation device 102 of the system 100 described above, comprises a clamp 502, a clamping ring 504 and a plurality of spheres 506. The spheres 506 are housed in the clamping ring 504 such that when the clamp 502 is moved relative to the clamping ring 504 such that the clamp 502 and the clamping ring 504 engage one another, the spheres 506 move radially inward from a first configuration in which a cable 104 can pass slidably therethrough to a second configuration in which a portion of the cable 104 passing through the device 500 is compressed between the spheres 506 fixing the cable 104 at a desired position relative thereto.

The clamp 502 includes a head 508, a body 510 and a lumen 512 extending therethrough for slidably accommodating the cable 104. The head 508 extends from a proximal end 514 of the body 510 and may be sized and shaped to engage the distal end 156 of the inner sleeve 144. In a preferred embodiment, the head 508 is, for example, hexagonally shaped to accommodate a hexagonally shaped recess of the distal end 156. A recess 516 at a distal end 518 of the body 510 includes an angled inner surface 520 such that a diameter at the distal end 518 is greater than a diameter at a proximal end 522 of the recess 520. The angled surface 520 of the recess 516 comes into contact with the plurality of spheres 506 as the device 500 moves from the first configuration to the second configuration so that the angled surface 520 pushes the spheres radially inward compressing the portion of the cable 104 passing therebetween. An outer surface 524 of the body 510 may include a threading (not shown) or other mating mechanism such that the body 510 of the clamp 502 engages the clamping ring 504.

The clamping ring 504 includes a channel 526 extending therethrough. The channel 526 includes a first portion 528 and a second portion 530, the first portion 528 being distal of the second portion 530. The first portion 528 may include an angled inner surface 532 extending from a distal end 534 to a proximal end at a distal end 536 of the second portion 530. The distal end 534 is sized and shaped to slidably accommodate the cable 104. The second portion 530 may be sized and shaped to engage with the body 510 of the clamp 502. Thus, the second portion 530 may include a threading (not shown) or other mating mechanism for engaging with the body 510. An outer surface 538 of the clamping ring 504 may be shaped to mate with the distal end 146 of the outer sleeve 142.

In the first configuration, the spheres 506 may be substantially housed within the second portion 530 of the clamping ring 504. As the clamp 502 and the clamping ring 504 move relative to one another along a longitudinal axis of the device 500, moving from the first configuration to the second configuration such that the body 510 of the clamp 502 engages the second portion 530 of the clamping ring 504, the angled inner surface 520 of the clamp 502 comes into contact with the spheres 506, pushing the spheres 506 toward the angled surface 532 of the first portion 528. The angled surface 532 of the clamping ring 504 and the angled inner surface 520 of the clamp 502 thus push the spheres 506 radially inward toward one another compressing the cable 104 extending through the channel 526 and the lumen 512 and fixing the cable 104 at a desired position and/or tension. In a preferred embodiment, the device 500 includes four spheres 506. However, it will be understood by those of skill in the art that the device 500 may include any number of spheres 506 so long as the spheres may be pushed radially inward relative to a longitudinal axis of the device 500 to compress a portion of the cable 104 passing therebetween.

Figure 21:
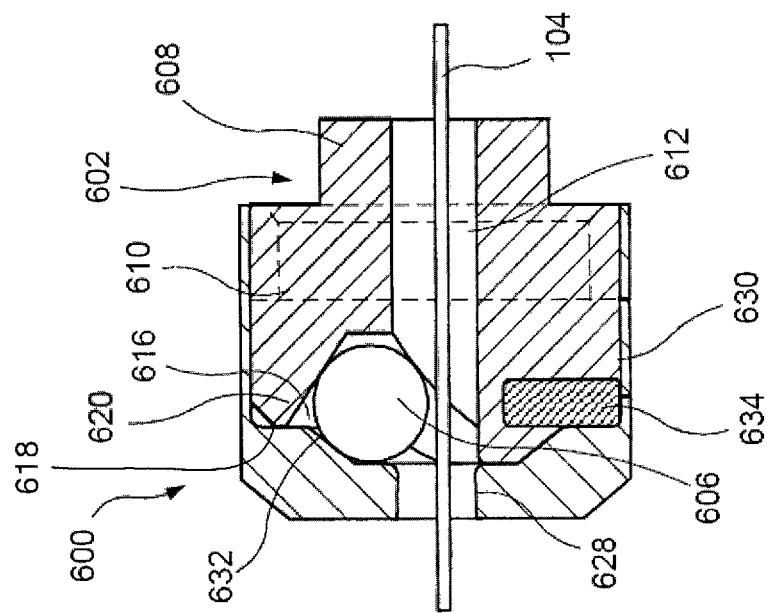
FIG. 21 shows a cross-sectional side view of the cable fixation device of FIG. 20.
Figure 20:
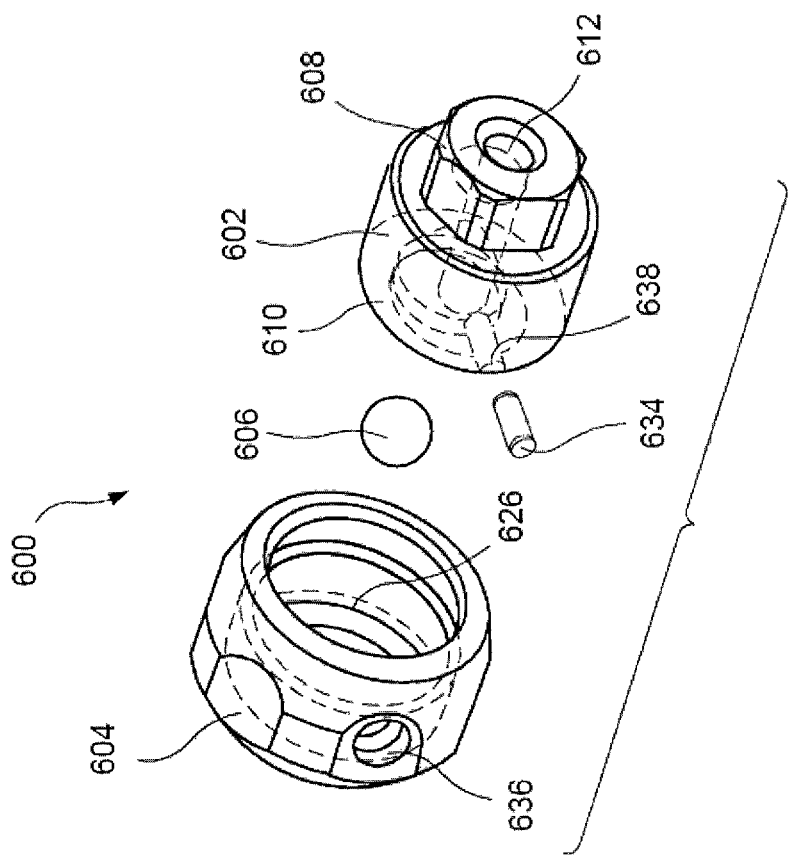
FIG. 20 shows an exploded perspective view of a cable fixation device according to a sixth exemplary embodiment of the present invention.

As shown in FIGS. 20-21, an alternate cable fixation device 600 includes a clamp 602 and a clamping ring 604 along with a sphere 606, which may be housed within the clamping ring 604. It will be understood by those of skill in the art that the device 600 may be used in the system 100, as described above, in substantially the same manner as the cable fixation device 102. The sphere 606 is movable between a first configuration in which the cable 104 may easily pass through the device 600 and a second configuration in which the sphere 606 is moved radially inward toward a center of a lumen 612 through which the cable 104 passes to clamp the cable 104 and fix it in position.

The cable fixation device 600 is substantially similar to the cable fixation device 500 described above, but includes a single sphere 606 rather than the plurality of spheres in the device 500. Similarly to the clamp 502, the clamp 602 includes a head 608, a body 610 and a lumen 612 extending therethrough. The clamp 602 also includes a recess 616 at a distal end 618 thereof with an angled surface 620 of the recess 616 configured to contact the sphere 606 to move the sphere 606 from the first configuration to the second configuration as will be described below.

Similarly to the clamping ring 504, the clamping ring 604 includes a channel 626 extending therethrough, including a first portion 628 and a second portion 630. The first portion 628 is sized and shaped to slidably accommodate the cable 104. The second portion 630 is sized and shaped to accommodate the body 610 of the clamp 602. In addition, the channel 626 further includes a notch 632 distal of the second portion 630, which is sized and shaped to accommodate the sphere 606 in the second configuration.

As will be understood by those of skill in the art, when the clamp 602 is moved relative to the clamping ring 604 such that the body 610 engages the second portion 630 of the channel 626, the body 610 is moved into the second portion 630 and the angled surface 620 contacts the sphere 606 moving the sphere radially inward into the notch 632 of the channel 626. Once in the notch 632, the device 600 is in the second configuration with the sphere 606 pressed against the portion of the cable 104 passing through the lumen 612 and the channel 626 gripping the cable 104 and fixing the device 600 in position along the cable 104. To fix the clamp 602 relative to the clamping ring 604, an insert 634 may be inserted into an opening 636 of the clamping ring 604 and a corresponding opening 638 in the clamp 602.

Figure 23:
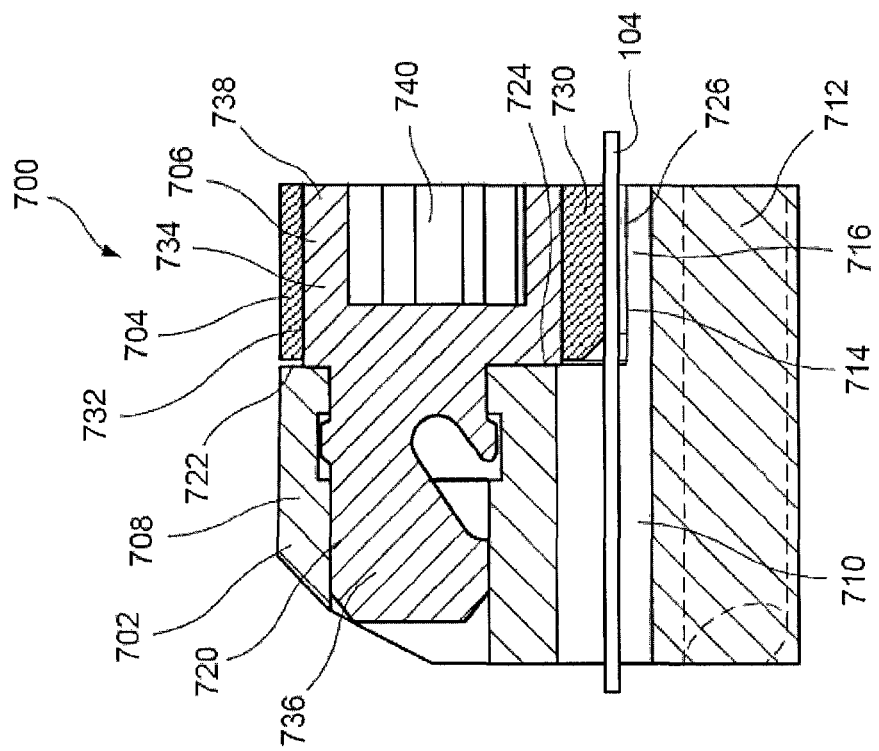
FIG. 23 shows a cross-sectional side view of the cable fixation device of FIG. 22.
Figure 22:
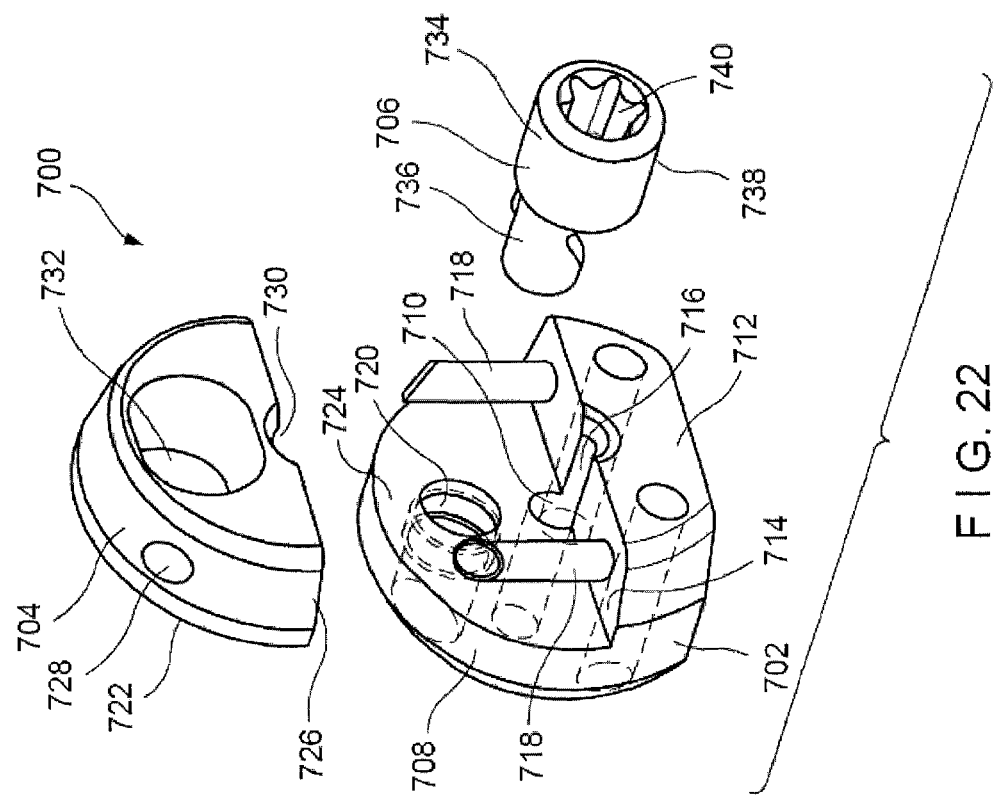
FIG. 22 shows an exploded perspective view of a cable fixation device according to a seventh exemplary embodiment of the present invention.

As shown in FIGS. 22-23, a cable fixation device 700 according to a further embodiment of the invention comprises a first element 702, a second element 704 and a screw 706. The device 700 may be used in the system 100, as described above, in place of the cable fixation device 102. The first element 702 and the second element 704 may be removably coupleable to one another such that the first and second elements 702, 704 are movable relative to one another between a first configuration in which the cable 104 is slidable therethrough and a second configuration in which the cable is gripped between the first and second elements 702 fixing the cable 104 in place relative to the device 700.

The first element 702 includes a body portion 708 and a lumen 710 extending therethrough, the lumen 710 being sized and shaped to slidably accommodate the cable 104. The first element 702 also includes a shoulder 712 extending proximally from the body portion 708, on one side of the lumen 710 such that a surface 714 of the shoulder 712 includes a groove 716 co-axial with the lumen 710. The first element 702 may further include a pair of prongs 718 extending laterally from the surface 714, on either side of the groove 716, for engaging the second element 704. The first element 702 also includes an opening 720 for engaging a portion of the screw 706. The opening 720 may include a threading (not shown) or other mating mechanism for engaging with the screw 706 as would be understood by those skilled in the art.

The second element 704 is sized and shaped to engage the first element 702. For example, the second element 704 may include a distal surface 722 for abutting a proximal surface 724 of the first element, and a lateral surface 726, which may be substantially perpendicular to the distal surface 722 for facing the surface 714 of the shoulder 712 of the first element 702. The lateral surface 726 includes a pair of holes 728 extending laterally therethrough for accommodating the prongs 718. Thus, the first and second elements 702, 704 may engage one another via the prongs 718 and the holes 728. The lateral surface 726 also includes a groove 730, which may be substantially co-axial with the lumen 710 when the first and the second elements 702, 704 are engaged with one another. Thus, it will be understood by those of skill in the art that the first and second elements 702, 704 engage one another such that the cable 104 may be slid through the lumen 710 between the grooves 716, 730 of the first and second elements 702, 704. Further, the second element 704 also includes an opening 732 for accommodating a portion of the screw 706. The opening 732 may include a threading (not shown) or other mating mechanism for engaging with the screw 706.

The screw 706 includes a head portion 734 and a shaft portion 736. The head portion 706 includes a recess 740 at a proximal end 738 thereof for mating with a driving tool. It will be understood by those of skill in the art, however, that the head portion 734 of the screw 706 may include any recess or protrusion so long as the head portion 734 is matable with a driving tool. The shaft portion 736 extends distally from the head portion 734, but includes a longitudinal axis off-center from a longitudinal axis of the head portion 734. Thus, the longitudinal axis of the head portion 734 is parallel to the longitudinal axis of the shaft portion 736. The head portion 734 may be sized and shaped to engage the opening 732 of the second element 704 while the shaft portion 736 may be sized and shaped to engage the opening 720 of the first element 702. Each of the head portion 734 and the shaft portion 736 may include a threading (not shown) or other mating mechanism for engaging with the openings 732, 720, respectively.

In the first configuration, the screw 706 is positioned within the openings 720, 732 such that the shaft 736 is within the opening 720 of the first element 702 and the head portion 734 is within the opening 730 of the second element 704. Additionally, the first and second elements 702, 704 are engaged with one another with the prongs 718 inserted into the holes 728 and the cable 104 slidably inserted into the lumen 710 between the grooves 716, 730. In the second configuration, the screw 706 is rotated approximately 180 degrees such that the off-set shaft portion 736 is shifted to a radially opposite position, moving the second element 704 relative to the first portion 702 so that the lateral surface 726 abuts the surface 714 of the shoulder 710. Upon abutment of the lateral surface 726 of the second element 704 and the surface 714 of the first element 702, a space between the grooves 716, 730 is decreased such that the cable 104 passing therebetween is gripped between the first and second elements 702, 704, fixing the device 700 along the cable 104.

As shown in FIGS. 24-25, a cable fixation device 800 according to a still further embodiment of the invention comprises a body portion 802 and a screw 804. The cable fixation device 800 may be used in the system 100, as described above, in place of the cable fixation device 102. The body portion 802 includes a lumen 806 extending therethrough for slidably accommodating the cable 104. The body portion 802 further includes an opening 808 extending therethrough for accommodating the screw 804. The opening 808 includes a first portion 810 and a second portion 812. The first portion 810 is sized and shaped to accommodate a shaft portion 814 of the screw 804 while the second portion 812 is sized and shaped to accommodate a head portion 816 of the screw 804. The second portion 812 is open at an edge 822 of the body portion 802 and extends partially into the lumen 806 such that a proximal portion 818 of the lumen 806 is open on one side.

The screw 804 includes the head portion 816 and the shaft portion 814, the shaft portion 814 extending distally from the head portion 816. The shaft portion 814 is offset from the head portion 816 such that a longitudinal axis of the shaft portion 814 is not aligned with a longitudinal axis of the head portion 814, but extends parallel to the longitudinal axis of the head portion 814. Thus, the screw 804 may be inserted into the body portion 802 in a first configuration, which allows the cable to be slidably inserted through the lumen 806, and rotated relative to the body portion 802 to a second configuration in which an outer surface 820 of the head portion 816 extends partially into the proximal portion 818 of the lumen 806 such that the cable 104 passing therethrough is gripped by the outer surface 820. The screw 804 may be rotated about the longitudinal axis of the shaft portion 814 (e.g., by approx. 180°) to move the head portion 816 from the first configuration in which the outer surface 820 of the head portion extends past the edge 822 of the body portion 802 to the second configuration in which the head portion 816 no longer extends past the edge 822, but rather extends into the proximal portion 818 of the lumen 806 gripping the cable 104 and fixing the device 800 in position relative thereto.

As shown in FIGS. 26-27, a cable fixation device 900 according to a ninth exemplary embodiment of the present invention, comprises a clamp 902, a clamping ring 904 and a damper 906. The cable fixation device 900 may be used in the system 100, as described above. The damper 906 may be housed within the clamping ring 904 and is movable between a first configuration and a second configuration. The clamp 902 includes a head 908 and a body 910 along with a lumen 912 extending therethrough. A distal portion 914 of the lumen 912 within the body 910 includes an angled inner surface 916 that contacts the damper 906 to move the damper 906 from the first configuration to the second configuration. Thus, it will be understood by those of skill in the art that a diameter of the lumen 912 is greater a distal end 924 of the clamp 902 than at a proximal end 926 of the distal portion 914 of the lumen 912. The head 908 may be adapted and configured to mate with a portion of the clamping tool 108 while the body 910 includes a threading (not shown) or other mating mechanism to engage with the clamping ring 904.

A channel 918 extending through the clamping ring 904 includes a first portion 920 sized and shaped to slidably accommodate the cable 104 therethrough and a second portion 922 sized and shaped to accommodate the body 910 of the clamp 902 in addition to the damper 906. The second portion 922 includes a threading (not shown) or other mating mechanism for engaging with the body 910 of the clamp 902. An outer surface 928 of the clamping ring 904 is sized and shaped to mate with a portion of the clamping tool 108. The damper 906 has a substantially rounded outer surface 930 including an angled surface 932, which flares radially outward as the angled surface 932 extends from a proximal end 934. The outer surface 930 may also include a pair of lateral surfaces 931 on opposite sides of the damper 906, which engage corresponding surfaces within the first portion 920 of the channel 918 of the clamping ring 904 to prevent rotation of the damper 906 relative to the clamping ring 904. An inner surface 936 of the damper 906 may also be substantially rounded such that in the first configuration, the inner surface 936 is radially outward of the first portion 920.

To move the device 900 to the second configuration, the clamp 902 is rotated relative to the clamping ring 904 about a longitudinal axis of the device 900 so the clamp 902 and the clamping ring 904 move longitudinally relative to one another and the body 908 and the second portion 922 of the channel 918 engage one another. The angled surface 916 of the lumen 912 then comes into contact with the angled surface 932 of the damper 906, pushing the damper 906 radially inward such that a portion of the cable 104 passing through the lumen 906 and the channel 918 is gripped by the inner surface 936 of the damper 906.

Figure 29:
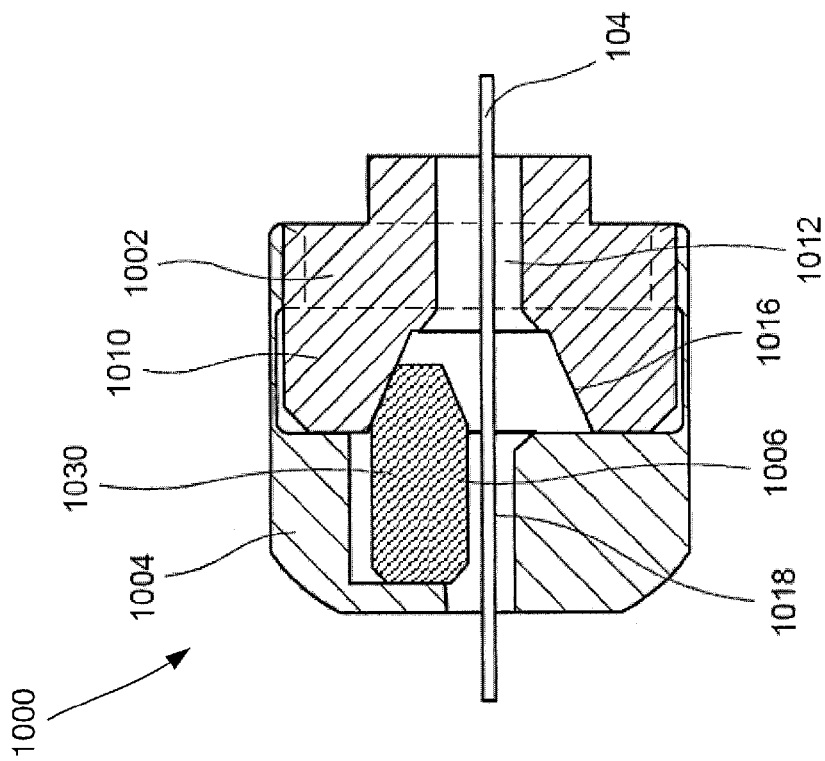
FIG. 29 shows a cross-sectional side view of the cable fixation device of FIG. 28.
Figure 28:
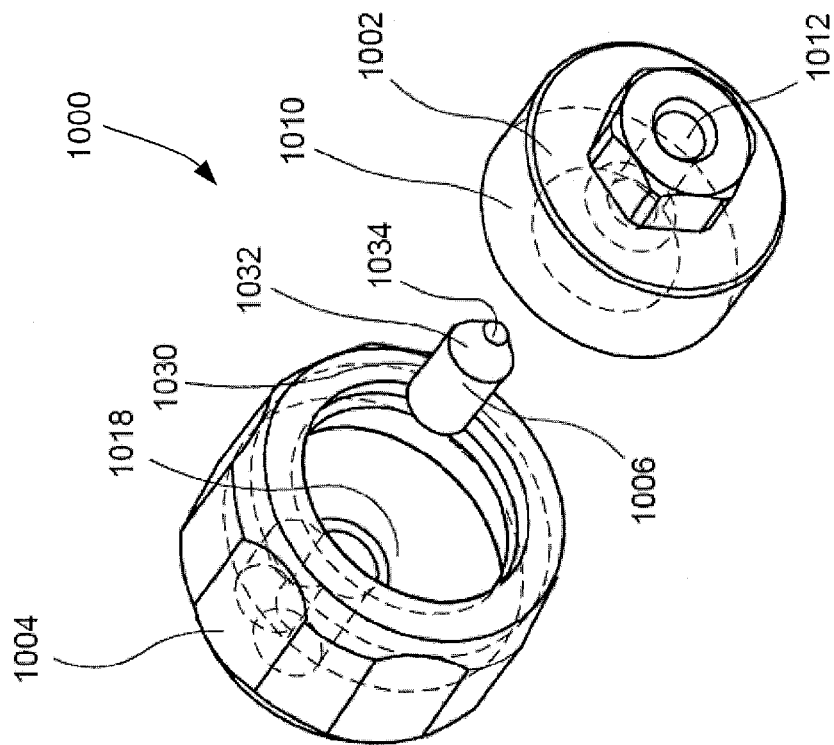
FIG. 28 shows an exploded perspective view of a cable fixation device according to a tenth exemplary embodiment of the present invention.

As shown in FIGS. 28-29, a cable fixation device 1000 according to another embodiment of the invention includes a clamp 1002, a clamping ring 1004 and a damper 1006. The cable fixation device 1000 may be substantially similar to the cable fixation device 900, as described above, except that the damper 1006 may be substantially longitudinal with an outer surface 1030 of the damper 1006 clamping a portion of the cable 104 passing through a channel 1018 of the clamping ring 1004 and a lumen 1012 of the clamp 1002. Similarly to the damper 906, the damper 1006 includes an angled surface 1032 at a proximal end 1034 thereof, which contacts an angled surface 1016 of the clamp 1002 as the clamp 1002 is rotated relative to the clamping ring 1004 so that a body 1010 of the clamp 1002 engages a portion of the channel 1018 of the clamping ring 1004. The angled surface 1016 of the clamp 1002 pushes the damper 1006 radially inward to clamp the cable 104, fixing the cable fixation device 1000 in a desired position along the cable 104.

As shown in FIGS. 30-31, a cable fixation device 1100 according to another embodiment of the invention comprises a clamp 1102, a clamping ring 1104 and a disk 1106. The cable fixation device 1100 may be used in the system 100, as described above, to fix the cable 104 at a desired tension and/or position. The disk 1106 is substantially housed within the clamping ring 1104 and is movable between a first configuration (shown in FIG. 30) in which the cable 104 is slidable therethrough and a second configuration (shown in FIG. 31) in which the cable 104 is fixed therein.

The clamp 1102 may include a head portion 1108, a body portion 1110 extending distally from the head portion 1108 and a lumen 1112 extending therethrough for slidably accommodating the cable 104. The head portion 1108 may include a threading 1114 for engaging a portion of the clamping ring 1104 and a driving element 1109 that may be engaged by a driving tool to move the clamp 1102 relative to the clamping ring 1104. For example, the driving element 1109 may be hexagonally shaped to engage with the inner sleeve 144 of the clamping tool 108. Alternatively, the driving element 1109 may be a recess formed at a proximal end of the head portion 1108. It will be understood by those of skill in the art that the driving element 1109 may be any recess or protrusion engagable by any driving tool such as, for example, the clamping tool 108 or a hex-driver.

The clamping ring 1104 includes a channel 1116 extending therethrough. A distal opening 1118 of the lumen 1116 may be sized and shaped to slidably accommodate the cable 104 while a proximal opening 1120 may be sized and shaped to accommodate the head portion 1108 of the clamp 1102. The proximal opening 1120 may include a threading 1122 for engaging the threading 1114 of the head portion 1108. The lumen 1116 may further include a shoulder 1124 along an inner surface 1126 thereof, the shoulder 1124 facilitating movement of the disk 1106 between the first configuration and the second configuration. The shoulder 1124 extends from the inner surface 1126 such that a diameter of the lumen 1116 distal of the shoulder 1124 is smaller than a diameter of the lumen proximal of the shoulder 1124. The diameter of the lumen 1116 distal of the shoulder 1124 is smaller than a diameter of the disk 1106. In a preferred embodiment, an outer surface 1105 of the clamping ring 1104 may be hexagonally shaped such that the outer surface 1105 is engagable with a hexagonally shaped recess 148 of the outer sleeve 142 of the clamping tool 108. However, it will be understood by those of skill in the art that the outer surface 1105 may be any of a variety of shapes so long as the outer surface is engagable with a correspondingly shaped distal end 146 of the outer sleeve 142.

The disk 1106 is housed within the clamping ring 1104 within the lumen 1106. The disk 1106 is substantially planar and includes an opening 1128 extending therethrough. In the first configuration, the disk 1106 is substantially perpendicular to a longitudinal axis of the lumen 1116 such that the opening 1128 is coaxial with the distal opening 1118 of the lumen 1116. As the device 1100 is moved into the second configuration, the clamp 1102 is moved longitudinally relative to the clamping ring 1104 via for example, rotation about the longitudinal axis, such that the clamp 1102 engages the clamping ring 1104. A distal end 1130 of the body portion 1110 distally pushes the disk 1106 such that the disk 1106 is moved distally within the clamping ring 1104 until the disk 1106 comes into contact with the shoulder 1124. A portion of the disk 1106 thus cannot move distally beyond the shoulder 1124 such that the disk 1106 is tilted at an angle relative to the longitudinal axis, into the second configuration. Once tilted, a surface 1132 of the opening 1128 of the disk 1106 comes into contact with the cable 104 such that the cable 104 is clamped by the opening 1128, fixing the device 1100 in position along the cable 104. The clamp 1102 and the clamping ring 1104 may be fixed relative to one another via an engagement between the threads 1108 of the clamp 1102 and the threads 1122 of the clamping ring 1104.

As shown in FIGS. 32-33, a cable fixation device 1200 according to a twelfth exemplary embodiment of the present invention, may be substantially similar to the cable fixation device 1100, described above. Similarly, the cable fixation device 1200 comprises a clamp 1202 and a clamping ring 1204 that are movably engaged via, for example, a thread. However, rather than a disk, the cable fixation device includes a shaped sheet 1206, which may be shaped into a Z or zig-zag shape such that an opening 1228 extends through multiple portions of the sheet 1206. Similarly to the cable fixation device 1100, the sheet 1206 is substantially housed within the clamping ring 1204 and is movable between a first configuration, shown in FIG. 32, in which the opening 1228 is substantially co-axial with a distal opening 1218 of the clamping ring 1204, to a second configuration, shown in FIG. 33, in which the sheet 1206 is bent by a distal end 1230 of the clamp 1202 such that inner surfaces 1232 of the opening 1228 come into contact with the cable 104 such that the cable 104 is clamped by the sheet 1206, fixing the cable fixation device 1200 in a desired position along the cable 104. It will be understood by those of skill in the art that the sheet 1206 is movable between the first and the second configuration in a spring-like manner.

Figure 34:
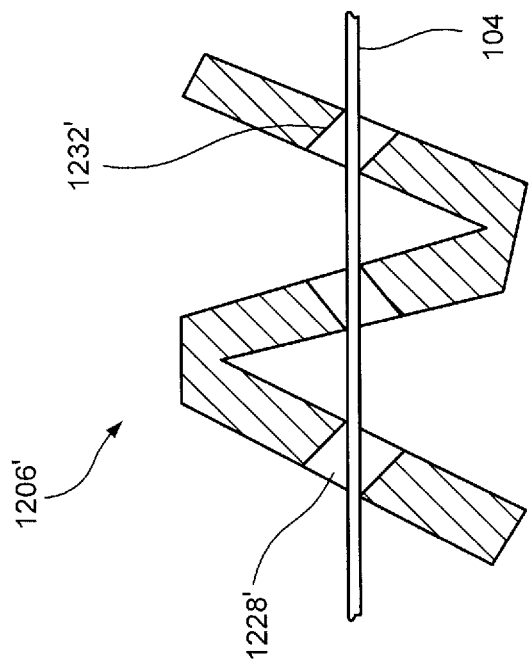
FIG. 34 shows an alternate embodiment of a sheet of the cable fixation device of FIG. 31, in a first configuration.
Figure 35:
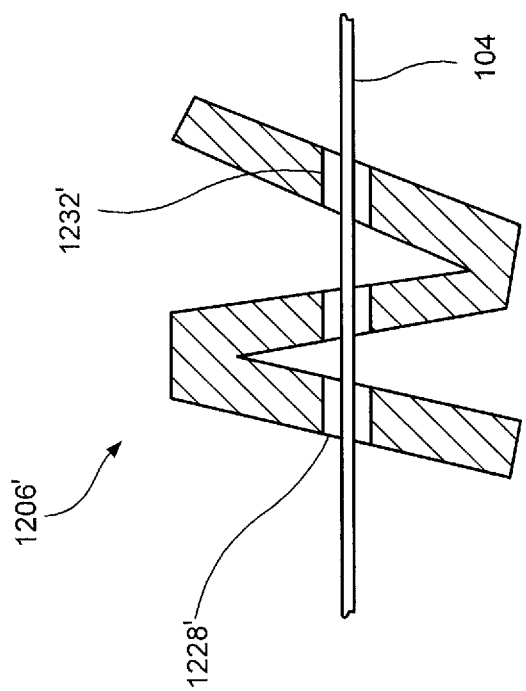
FIG. 35 shows the sheet of FIG. 34, in a second configuration.

Alternatively, the cable fixation device 1200 may include a sheet 1206', as shown in FIGS. 34-35, to work substantially oppositely of the sheet 1206, as described above. The sheet 1206' may be substantially similar to the sheet 1206, shaped in a Z or zig-zag shape and including an opening 1228' extending through multiple portions of the sheet 1206'. However, in a first configuration, as shown in FIG. 34, the sheet 1206' is held in a bent or compressed configuration by the distal end 1230 of the clamp 1202 such that the opening 1228' is substantially coaxial with the distal opening 1218 of the clamping ring 1204. Thus, the clamp 1202 is moved proximally relative to the clamping ring 1204 to decompress the sheet 1206' into a second configuration, shown FIG. 35, such that an inner surface 1232' of the opening 1228' comes into contact with the cable 104, clamping the cable 104 at a desired position along the cable 104.

As shown in FIG. 36, a cable fixation device 1300 according to another embodiment of the present invention comprises a body 1302 and an insert 1322. The body 1302 includes a first lumen 1304 extending therethrough from a proximal end 1308 to a distal end 1310 of the body 1302. The body 1302 further includes a second lumen 1306 extending from the first lumen 1304 to an outer surface 1312 of the body 1302 at an angle relative to the first lumen 1304 such that the second lumen 1306 is in communication with the first lumen 1304. A first portion 1314 of the first lumen 1304 extends from the distal end 1310 to a first end 1318 of the second lumen 1306 while a second portion 1316 extends from the first end 1318 of the second lumen 1306 to the proximal end 1308. The second end 1320 of the second lumen 1306 is proximal of the first end 1318.

In one embodiment, the first lumen 1304 may be sized and shaped to slidably accommodate the cable 104 such that the cable 104 may be inserted from the distal end 1310 proximally past the proximal end 1308. The second lumen 1306 is sized and shaped to accommodate the insert 1322. The second lumen 1306 may include a threading at least partially therealong. Once a desired tension has been applied to the cable 104 and the body 1302 is moved to a desired position along the cable 104, the insert 1322 is inserted through the second lumen 1306 until a distal end 1324 of the insert 1322 contacts and compresses the cable 104, fixing the cable fixation device 1300 in position along the cable 104. The insert 1322 may be, for example, a screw including a threading along a length thereof for engaging the threading of the second lumen 1306. In another embodiment, as shown in FIG. 37, the cable 104 may be inserted through the first portion 1314 of the first lumen 1304 and the second lumen 1306. In this case, as will be understood by those of skill in the art, the second portion 1316 of the first lumen 1304 is adapted and configured to receive the insert 1322. The second portion 1316 of the first lumen 1304 may therefore include a threading or any other suitable structure for locking the insert 1322 in a desired position therein. The outer surface 1312 of the body 1302 may be adapted according to clinical requirements. For example, as shown in FIGS. 36 and 37, the body 1302 may be substantially cylindrical with an angled tip to deflect the cable 104 from the first lumen 1304 into the second lumen 1306.

In an alternate embodiment, however, as shown in FIGS. 38-40, a cable fixation device 1300' that is substantially similar to the device 1300 may include a substantially cone-shaped body 1302' and an insert 1322'. A first lumen 1304' extends from a substantially planar proximal surface 1308' to a substantially planar distal surface 1310'. As shown, a diameter of the distal surface 1310' may be smaller than a diameter of the proximal surface 1308'. The body 1302' further includes a second lumen 1306' extending from the first lumen 1304' to the proximal surface 1308' such that the second lumen 1306' is at an angle relative to the first lumen 1304'. As described above in regard to the cable fixation device 1300, the cable 104 may be inserted through the body 1302' from the distal end 1310' through the first lumen 1304' to extend proximally from the proximal end 1308' of the first lumen 1304', as shown in FIGS. 38 and 39. In an alternate embodiment, as shown in FIG. 40, the cable 104 may be inserted through a first portion 1314' of the first lumen 1304' and the second lumen 1306' with the insert 1322' inserted through a second portion 1316' of the first lumen 1304' to fix the cable fixation device 1300' at a desired tension and position along the cable 104.

Figure 41:
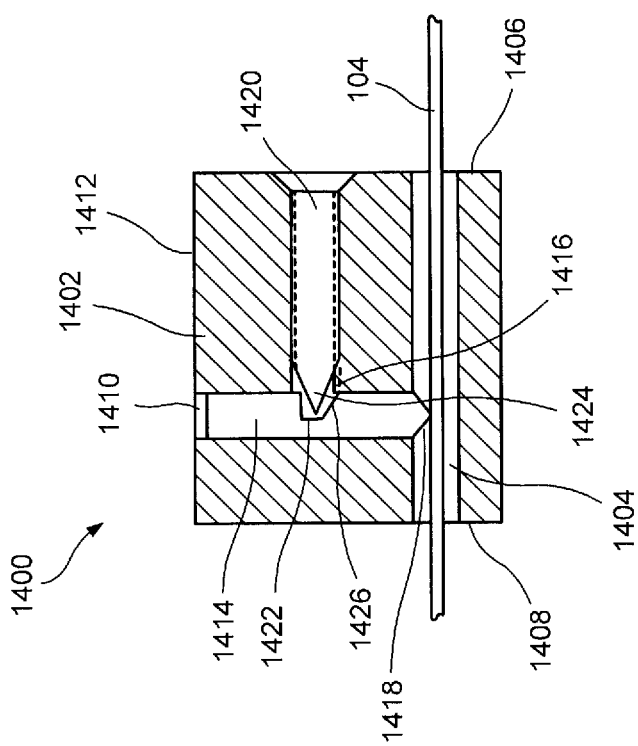
FIG. 41 shows a cross-sectional side view of a fourteenth exemplary embodiment of a cable fixation device according to the present invention.

As shown in FIG. 41, a cable fixation device 1400 comprises a body 1402 and an insert 1420. The body 1402 includes a first lumen 1404 extending therethrough from a proximal end 1406 to a distal end 1408. The body further includes an opening 1410 extending laterally from the first lumen 1404 to an outer surface 1412 of the body 1402 for accommodating a bolt 1414. The bolt 1414 is movable from a first configuration in which a distal end 1418 of the bolt 1414 does not extend into the first lumen 1404 to a second configuration in which the distal end 1418 of the bolt extends into the first lumen 1404. A second lumen 1416 extends substantially parallel to the first lumen 1404, extending from the opening 1410 to the proximal end 1406. The second lumen 1416 is sized and shaped to accommodate an insert 1420, which, in a preferred embodiment, is a screw. Thus, the second lumen 1416 may include a threading along an inner surface thereof for engaging a threading of the insert 1420.

The bolt 1414 includes a lateral groove 1422 for accommodating a distal end 1424 of the insert 1420, the lateral groove including an angled surface 1426 for engaging the distal end 1424 such that the bolt 1414 may be moved from the first configuration to the second configuration. The angled surface 1426 may be approximately 45° such that, in the first configuration, the distal end 1424 contacts an end of the angled surface 1426 closest to the proximal end of the insert 1420. As the insert 1420 is driven distally through the second lumen 1416, the distal end 1424 moves along the angled surface 1426 forcing the bolt 1420 through the opening 1410 into the first lumen 1404, into the second configuration in which it compresses the cable 104 and locks it in place. It will be understood by those of skill in the art that an outer surface 1412 of the body 1402 may be adapted as desired or clinically required. It will also be understood by those of skill in the art that the distal end 1418 of the bolt 1414 may also be adapted as desired.

Figure 42:
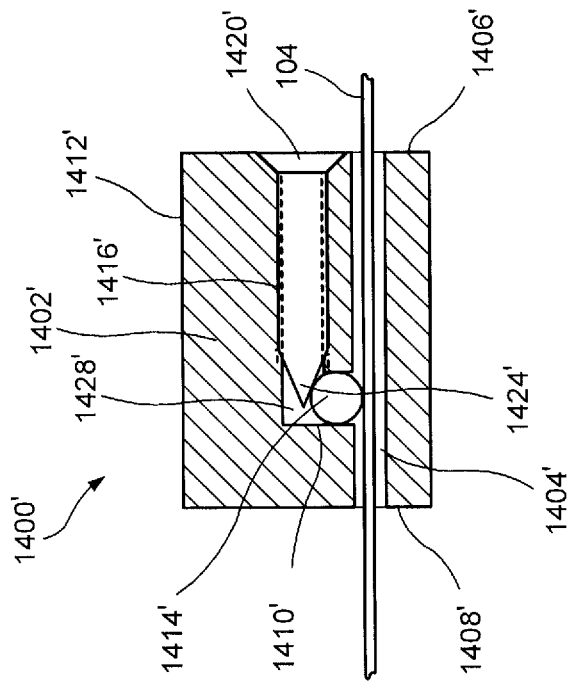
FIG. 42 shows a cross-sectional side view of an alternate embodiment of the cable fixation device of FIG. 41.

As shown in FIG. 42, a cable fixation device 1400' may be substantially similar to the cable fixation device 1400, comprising a body 1402' and an insert 1420'. The body 1402' includes a first lumen 1404' extending from a proximal end 1406' to a distal end 1408' and a second lumen 1416' substantially similar to the second lumen 1416. An opening 1410', however, does not extend to an outer surface 1412' of the body 1402', but rather extends laterally from the first lumen 1404' to a first end 1428' of the second lumen 1416'. Additionally, rather than a bolt 1414, the cable fixation device 1400' includes a contacting member 1414' (e.g., a sphere) housed within the opening 1410'. The contacting member 1414' is movable from a first configuration in which it does not extend into the first lumen 1404' to a second configuration in which it does extend into the first lumen 1404'. The insert 1420' is insertable into the second lumen 1416' such that a distal end 1424' of the insert 1420' contacts the contacting member 1414', pushing the contacting member 1414' to the second configuration compressing the cable 104 and locking it in place at a desired location and tension in the same manner described above.

In the first configuration, the cable 104 is insertable through the first lumen 1404. The cable 104 may be tensioned and the body 1402 positioned along the screw as desired. Once in the desired position, the insert 1420 is driven distally into the second lumen 1416 via, for example, rotation about a longitudinal axis such that threading of the insert engages the threading of the second lumen. As the distal end 1424 engages the angled surface 1426, the bolt 1414 is driven into the second configuration with the distal end 1418 of the bolt 1414 compressing the cable 104, fixing the cable fixation device 1400 in the desired position along the cable 104.

As shown in FIG. 43, a cable fixation device 1500 substantially similar to the cable fixation devices 200, 300 described above comprises a clamp 1502 and a clamping ring 1504 rotatable relative to one another to move the cable fixation device 1500 from a first configuration to a second configuration. Substantially similarly to the clamps 202, 302, the clamp 1502 includes a head 1506, a body 1508 and a lumen 1510 extending therethrough. The body 1508 includes, for example, a threading 1512 for engaging the clamping ring 1504. Similarly to the clamping ring 204, 304, the clamping ring 1504 includes a channel 1516 extending therethrough with a first portion 1518 sized and shaped to accommodate the cable 104 and a second portion 1520 for accommodating the body 1508 of the clamp. The second portion 1520 includes, for example, a threading 1522 for engaging the threading 1512 of the body 1508.

In the first configuration the lumen 1510 of the clamp 1502 and the channel 1516 of the clamping ring 1502 are substantially aligned so that the cable may be easily slid therethrough. The clamping ring 1504 may then be rotated relative to the clamp 1502, approximately 180°, to move the cable fixation device 1500 into the second configuration in which the lumen 1510 and the channel 1516 are offset and no longer aligned such that the cable 104 is gripped therebetween locking the cable 104 in a desired position at a desired tension.

As shown in FIG. 44, a cable fixation device 1500' according to a further embodiment of the invention is substantially similar to the cable fixation device 1500 with a clamp 1502' and a clamping ring 1504'. The clamp 1502' and the clamping ring 1504' are substantially similar to the clamp 1502 and clamping ring 1504 except for an engaging mechanism thereof which will be described in more detail below. Rather than a threading along a body 1508' of the clamp 1502' and a threading along a second portion 1520' of a channel 1516' of the clamping ring 1504', the clamp 1502' and the clamping ring 1504' engage one another via a snap ring 1524' received within a groove 1512' extending about a circumference of the body 1508 and a corresponding groove 1522' of the channel 1516' such that the clamp 1502' and the clamping ring 1504' may be "snapped" together. It will be understood by those of skill in the art that the ring shape of the snap ring 1524' permits rotation of the clamping ring 1504' relative to the clamp 1502' such that the cable fixation device 1500' may be moved between a first configuration and a second configuration to lock the cable 104, as described above in regard to the cable fixation device 1500.

Figure 45:
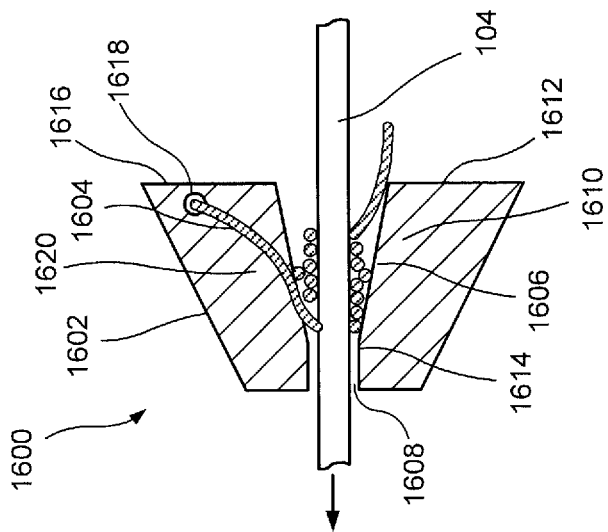
FIG. 45 shows a cross-sectional side view of a cable fixation device according to a sixteenth exemplary embodiment of the present invention, in a first configuration.
Figure 46:
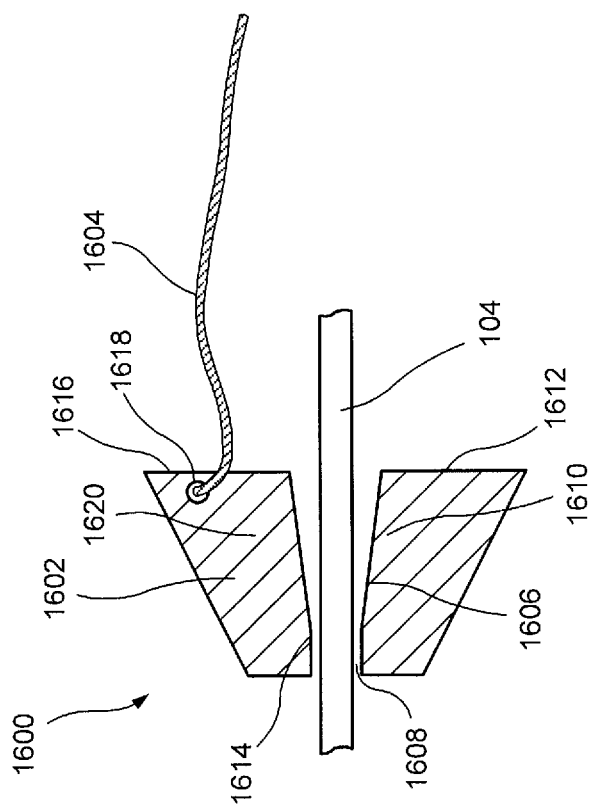
FIG. 46 shows a cross-sectional side view of the cable fixation device of FIG. 45, in a second configuration.

A cable fixation device 1600, as shown in FIGS. 45-46, comprises a body 1602 and a filament 1604 attached to a portion of the body 1602. The body 1602 may be substantially ring-shaped, including a lumen 1606 extending therethrough. The lumen 1606 may be substantially conical, including a first portion 1608 sized and shaped to slidably accommodate the cable 104 and a second portion 1610 including an angled surface 1620 extending from an end of the first portion 1608 with a diameter of the second portion 1610 at a proximal end 1612 being greater than a diameter of the second portion 1610 at a distal end 1614. The filament 1604 is attached to the body 1602. The filament 1604 may be attached to the body 1602 via any attachment mechanism such as, for example, knotting the filament 1604 through an opening 1618 proximate a proximal end 1616 of the body 1602.

In use, the cable 104 is slid through the lumen 1606 through the first portion 1608 to extend proximally past the second portion 1610. Once a desired tension has been applied to the cable 104 and the body 1602 is positioned over the cable 104 at a desired position, the filament 1604 is wound around the cable 104. The filament 1604 may be wound around the cable 104 as many times as desired and may also be wound around the cable 104 so that the filament 1604 overlaps upon itself, increasing a diameter of the wound filament 1604. However, it will be understood by those of skill in the art that the greater the number of times the filament 1604 is wound, the greater the fixation of the cable fixation device 1600 over the cable 104 will be. Once the filament 1604 has been wound as desired, the filament 1604 may be knotted or tied to prevent the filament from unwinding. Upon release of the cable 104 and the filament 1604, tension in the cable 104 urges the cable 104 distally along with the wound filament 1602 to move distally until the wound filament 1604 abuts the distal end 1615 of the second portion 1610 of the lumen 1606, preventing any further movement, and fixing the cable fixation device 1600 over the cable 104. It will be understood by those of skill in the art that the cable fixation device 1600 is fixed over the cable 104 via the conically shaped lumen 1606.

Figure 47:
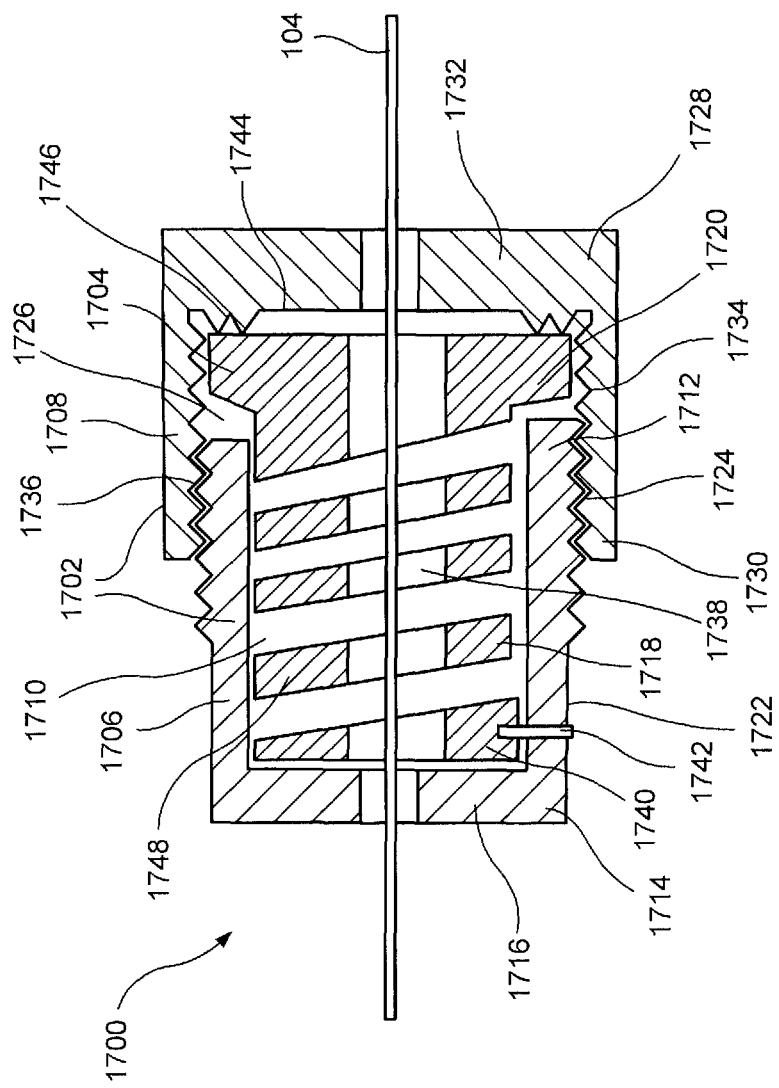
FIG. 47 shows a cross-sectional side view of a cable fixation device according to a seventeenth exemplary embodiment of the present invention.

As shown in FIG. 47, a cable fixation device 1700 according to another embodiment of the invention comprises a body 1702 and a spiral screw 1704 (e.g. a spring screw). The body 1702 further comprises a first member 1706 and a second member 1708 engaged to one another with the spiral screw 1704 housed substantially therewithin. The first member 1706 includes a lumen 1710 extending therethrough from a proximal end 1712 to a distal end 1714 of the first member 1706. The lumen 1710 is sized and shaped to accommodate a shaft portion 1718 of the spiral screw 1704. The first member 1706 further includes a shoulder 1716 at the distal end 1714 extending radially inward with an opening of the lumen 1710 at the distal end 1714 being smaller than an opening of the lumen 1710 at the proximal end 1712. An outer surface 1722 of the proximal end 1712 includes a threading 1724 thereaolong for engaging the second member 1708.

The second member 1708 also includes a lumen 1726 extending therethrough from a proximal end 1728 to a distal end 1730. The proximal end 1728 includes a shoulder 1732 extending radially inward such that an opening at the proximal end 1728 of the lumen 1726 is smaller than an opening of the lumen 1726 at the distal end 1730. The lumen 1726 is sized and shaped to accommodate the proximal end 1712 of the first member 1706 and a head portion 1720 of the spiral screw 1704. An inner surface 1734 of the lumen 1726 includes a threading 1736 for rotatably engaging the threading 1724 of the first member 1706. An inner surface 1744 of the shoulder 1732 may include teeth 1746 to grip the head portion 1720 of the spiral screw 1704 to prevent rotation of the head portion 1720 relative to the second member 1708.

The spiral screw 1704 includes the head portion 1720 and the shaft portion 1718 extending distally therefrom. The shaft portion 1718 is substantially spiral-shaped with a lumen 1738 of the screw 1704 extending through the screw 1704, radially within each of the spirals 1748 of the shaft portion 1718. A distal end 1740 of the shaft portion is fixed to the first member 1706 of the body 1702, preventing the distal end 1740 of the shaft portion 1718 from rotating relative to the body 1702. The distal end 1740 may be fixed to the first member 1706 via, for example, a pin 1742 extending through both the first member 1706 and the distal end 1740 of the spiral screw 1704.

Since the second member 1708 engages the head portion 1720 preventing relative movement therebetween and the first member 1706 engages the distal end 1740 of the shaft portion 1718 preventing relative movement therebetween, it will be understood by those of skill in the art that rotation of the second member 1708 relative to the first member 1706 rotates the head portion 1720 of the spiral screw 1704 relative to the shaft portion 1718. As the head portion 1720 rotates relative to the shaft portion 1718, the spirals 1748 are wound tighter such that a size of the lumen 1738 extending radially within the spirals 1748 is decreased, thereby clamping the cable 104 extending therethrough. Thus, it will be understood by those of skill in the art that rotation of the second member 1708 relative to the first member 1706 clamps the cable 104, fixing the cable fixation device 1700 at a desired tension and position along the cable 104.

Figure 48:
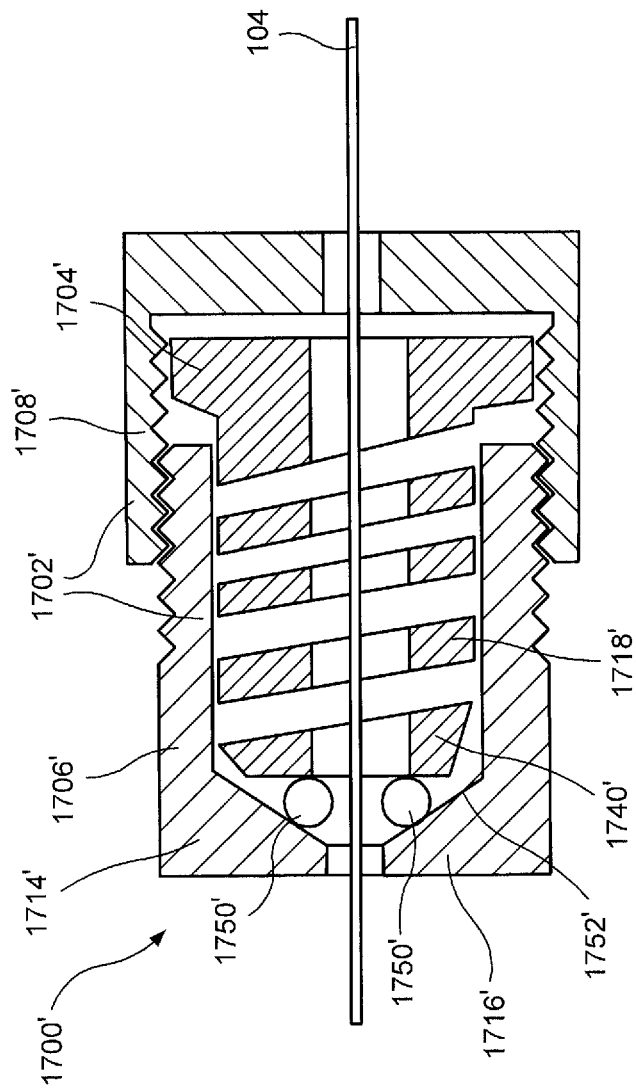
FIG. 48 shows a cross-sectional side view of another embodiment of the cable fixation device of FIG. 47.

As shown in FIG. 48, a cable fixation device 1700' may be substantially similar to the cable fixation device 1700, as described above. The cable fixation device 1700', however, in addition to a body 1702' and a spiral screw 1704' further includes a plurality of contacting members 1750' (e.g., spheres) that abut a distal end 1740' of the spiral screw 1704'. One embodiment of the invention includes three to six the contacting members 1750'. The body 1702' is substantially similar to the body 1702, including a first member 1706' and a second member 1708' rotatably engaged to one another to house the spiral screw 1704' therewithin. Unlike the device 1700, however, the spiral screw 1704' is not fixed relative to either of the first and the second members 1706', 1708'. Additionally, the first member 1706' includes a shoulder 1716' at a distal end 1714' of thereof, which includes an angled surface 1752' engaging the contacting members 1750' and pushing them radially inward as the spiral screw 1704' is advanced distally to clamp the cable 104 extending through lumens 1710', 1726' of the body 1702'.

To clamp the cable 104 extending through the cable fixation device 1700', the second member 1708' is rotated relative to the first member 1706' compressing the spiral screw 1704' housed therewithin. As the spiral screw 1704' is compressed, a distally directed longitudinal force is exerted by the spring-like spiral screw 1704' so that the distal end 1740' of a shaft portion 1718' of the screw 1704', pushes the contacting members 1750' distally against the angled surface 1752' of the shoulder 1716' moving the contacting members 1750' to clamp the cable 104 therebetween, fixing the cable fixation device 1700' in a desired position along the cable 104.

Figure 50:
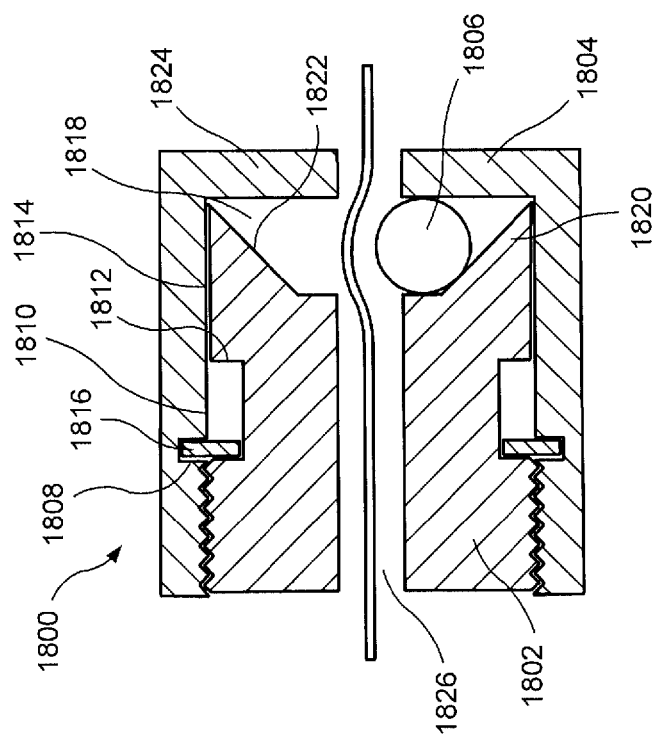
FIG. 50 shows a cross-sectional side view of the cable fixation device of FIG. 49, in a second configuration.
Figure 49:
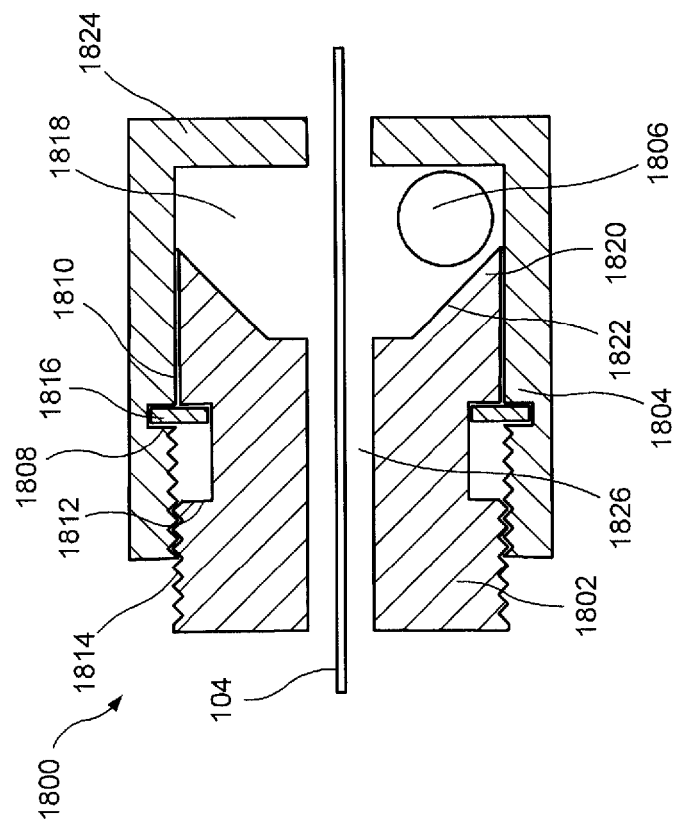
FIG. 49 shows a cross-sectional side view of a cable fixation device according to an eighteenth exemplary embodiment of the present invention, in a first configuration.

As shown in FIGS. 49-50, a cable fixation device 1800 comprises a clamp 1802, a clamping ring 1804 and at least one contacting member 1806. The clamp 1802 and the clamping ring 1804, include lumens 1826 and 1818, respectively, for accommodating the cable 104. The clamp 1802 and the clamping ring 1804 are engaged to one another for relative movement along a longitudinal axis of the device 1800 between first and second configurations. For example, the clamp 1802 and the clamping ring 1804 may be threadedly engaged to one another such that rotation or the clamping ring 1804 relative to the clamp 1802 moves the clamping ring 1804 longitudinally relative to the clamp 1802. The clamp 1802 and the clamping ring 1804 may be further coupled to one another via, for example, a snap ring 1816 received within a groove 1808 along an inner surface 1810 of the clamping ring 1804 and a groove 1812 along an outer surface 1814 of the clamp 1802. The groove 1808 in the clamping ring 1804 may be only slightly larger than the snap ring 1816 while the groove 1812 in the clamp 1802 is substantially larger than the snap ring 1816 such that the clamping ring 1804 is longitudinally movable relative to the clamp 1802. It will be understood by those of skill in the art that the snap ring 1816 maintains the clamp 1802 and the clamping ring 1804 in a coupled configuration even when the clamp 1802 and the clamping ring 1804 are not threadedly engaged. It will also be understood by those of skill in the art that the clamp 1802 and the clamping ring 1804 may be engaged to one another by any of a variety of methods so long as the clamp 1802 and the clamping ring 1804 are longitudinally movable relative to one another between the first and second configuration.

The contacting member 1806 is housed substantially within the lumen 1818 of the clamping ring 1804 between a proximal end 1820 of the clamp 1802 and a proximal end 1824 of the clamping ring 1804. The proximal end 1820 of the clamp includes an angled surface 1822 which contacts the contacting member 1806 so that, as the clamping ring 1804 is moved longitudinally relative to the clamp 1802 from the first configuration, shown in FIG. 49 to the second configuration shown in FIG. 50, the contacting member 1806 is forced radially inward to clamp the cable 104 passing through the lumens 1826, 1818. Although the cable fixation device 1800 is shown as including a single contacting member 1806, it will be understood by those of skill in the art that the cable fixation device 1800 may include any number of contacting members 1806 such that the angled surface 1822 pushes all of the spheres radially inward to clamp the cable 104 therebetween.

A cable fixation device 1900 as shown in FIGS. 51-54, is substantially similar to the cable fixation device 1800 except as described below and includes a clamp 1902 and a clamping ring 1904 movably coupled to one another such that the clamp 1902 is positioned proximally of the clamp 1904. For example, the clamp 1902 and the clamping ring 1904 may be threadedly engaged to one another. It will be understood by those of skill in the art, however, that the clamp 1902 and the clamping ring 1904 may be engaged to one another via a variety of coupling mechanisms such as, for example, a snap ring. Rather than including the contacting member 1806, the cable fixation device 1900 comprises a disc-shaped spring 1906 such as, for example, a Benzing ring, housed substantially within the clamping ring 1904 between a distal end 1920 of the clamp 1902 and a distal end 1924 of the clamping ring 1904. The disc-shaped spring 1906 is movable between a first configuration, in which the disc-shaped ring 1906 is deformed, and a second configuration, in which the disc-shaped ring 1906 is compressed. The distal end 1920 of the clamp 1902 and the distal end 1924 of the clamping ring 1904 are substantially planar such that the distal ends 1920, 1924 may compress the disc-shaped spring 1906 in the second configuration.

Figure 54:
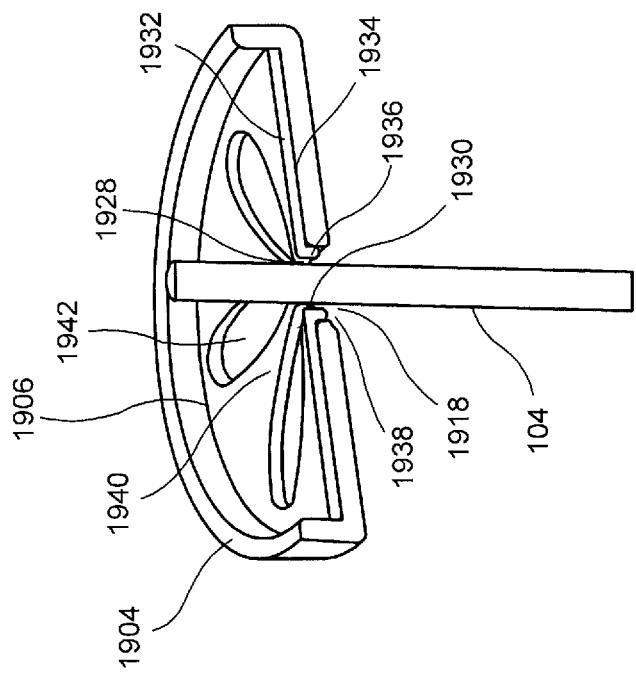
FIG. 54 shows a cross-sectional perspective view of the disc-shaped spring and clamping ring of FIG. 53.
Figure 53:
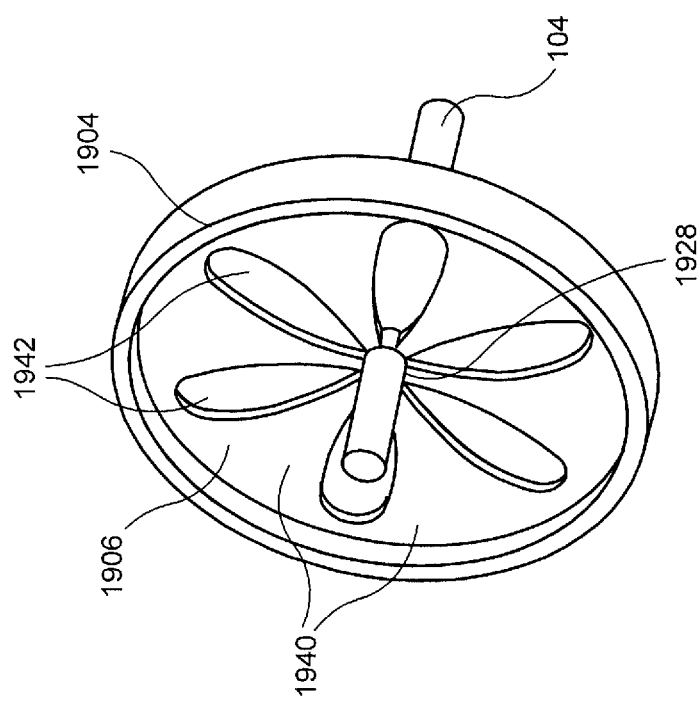
FIG. 53 shows a perspective view of a disc-shaped spring and a clamping ring of the cable fixation device of FIG. 51, in the first configuration.

The disc-shaped spring 1906, as shown in FIGS. 53-54, includes a substantially planar proximal surface 1932 and a substantially planar distal surface 1934 with an opening 1928 extending through a central portion therethrough for accommodating the cable 104. The disc-shaped spring 1906 includes a plurality of legs 1940 separated from one another circumferentially by openings 1942 with each of the legs 1940 including a protrusion 1936 extending along a radially inner wall 1930 thereof distally past the distal surface 1934. The disc-shaped spring 1906 is biased toward a first configuration (shown in FIG. 51) in which radially inner portions of the legs 1940 are bent proximally out of contact with the cable 104. In this first configuration, the cable 104 may be slid through the lumen 1918 of the clamping ring 1904 into the lumen 1926 of the clamp 1902. In the second configuration, the clamp 1902 is moved distally into contact with disc-shaped spring 1906, forcing the radially inward portions of the legs 1940 distally into a second, gripping configuration (shown in FIGS. 52-54) in which the protrusions 1936 contact and grip the cable 104, locking the position of the clamp 1902 on the cable and fixing a desired tension thereon in the same manner described above.

Specifically, in the first configuration, the distal ends 1920, 1924 of the clamp 1902 and the clamping ring 1904, respectively, are spaced sufficiently apart from one another such that the legs 1940 of the disc-shaped spring 1906 rotate under their natural bias proximally (counterclockwise as seen in FIG. 51) out of contact with the cable 104 to allow the cable 104 to pass through the opening 1928. In the second configuration, as shown in FIG. 52, the clamp 1902 and the clamping ring 1904 are moved relative to one another along a longitudinal axis such that the distal end 1920 of the clamp 1902 is moved longitudinally toward the distal end 1924 of the clamping ring 1904. The clamp 1902 and the clamping ring 1904 may be moved relative to one another via, for example, rotation with complementary threading translating the rotation of the clamping ring 1904 relative to the clamp 1902 into longitudinal movement therebetween. When in the second configuration, the disc-shaped spring 1906 is compressed between the distal ends 1920, 1924 of the clamp 1902 and the clamping ring 1904, respectively, moving the protrusions 1930 into the distal opening 1938 of the lumen 1918 of the clamping ring 1904 against the cable 104 to clamp the cable 104 therein. The bending of the disc-shaped spring 1906 causes the protrusions 1936 to press against the cable 104 passing through the lumen 1918 such that the fixation device 1900 is fixed in a desired position along the cable 104 at a desired tension.

As shown in FIGS. 55-57, a cable fixation device 2000 may be substantially similar to the cable fixation device 1900, as described above, comprising a clamp 2002 and a clamping ring 2004 that are movably coupled to one another via, for example, a thread or a snap ring. Rather than a disc-shaped spring 1906, however, the cable fixation device 2000 further comprises a pivotable lever 2006. The pivotable lever 2006 is housed substantially within the clamping ring 2004 substantially between a distal end 2020 of the clamp 2002 and a distal end 2024 of the clamping ring 2004. As shown in FIG. 57, the lever 2006 may be received within a longitudinal groove 2034 of the clamp 2002 and coupled to the clamp 2002 via a pin 2036, which permits pivoting of the lever 2006 relative to the clamp 2002. The lever 2006 is movable between a first configuration, as shown in FIG. 55, in which the cable 104 slidably passes through a lumen 2028 thereof, and a second configuration, as shown in FIG. 56, in which the cable 104 is clamped by an inner wall 2030 of the lever 2006.

The lever 2006 includes the lumen 2028 extending therethrough and a tab 2032 extending laterally therefrom. In the first configuration, the lumen 2028 is substantially aligned with the lumen 2026 of the clamping ring 2002 and the tab 2032 does not come into contact with the proximal end 2024 of the clamp 2004. In the second configuration, the clamp 2002 and the clamping ring 2004 are moved relative to one another, via rotation, for example, such that the distal end 2020 of the camp 2002 and the distal end 2024 of the clamping ring 2004 are moved longitudinally toward one another. The clamp 2002 and the clamping ring 2004 are moved relative to one another until the distal end 2024 of the clamping ring 2004 comes into contact with the tab 2032, pushing the tab 2032 such that the lever 2006 is moved into the second configuration. In the second configuration, the inner wall 2030 of the opening 2028 of the lever 2006 clamps the cable 104, fixing the cable fixation device 2000 over a desired position of the cable 104.

Figures 58, 59:
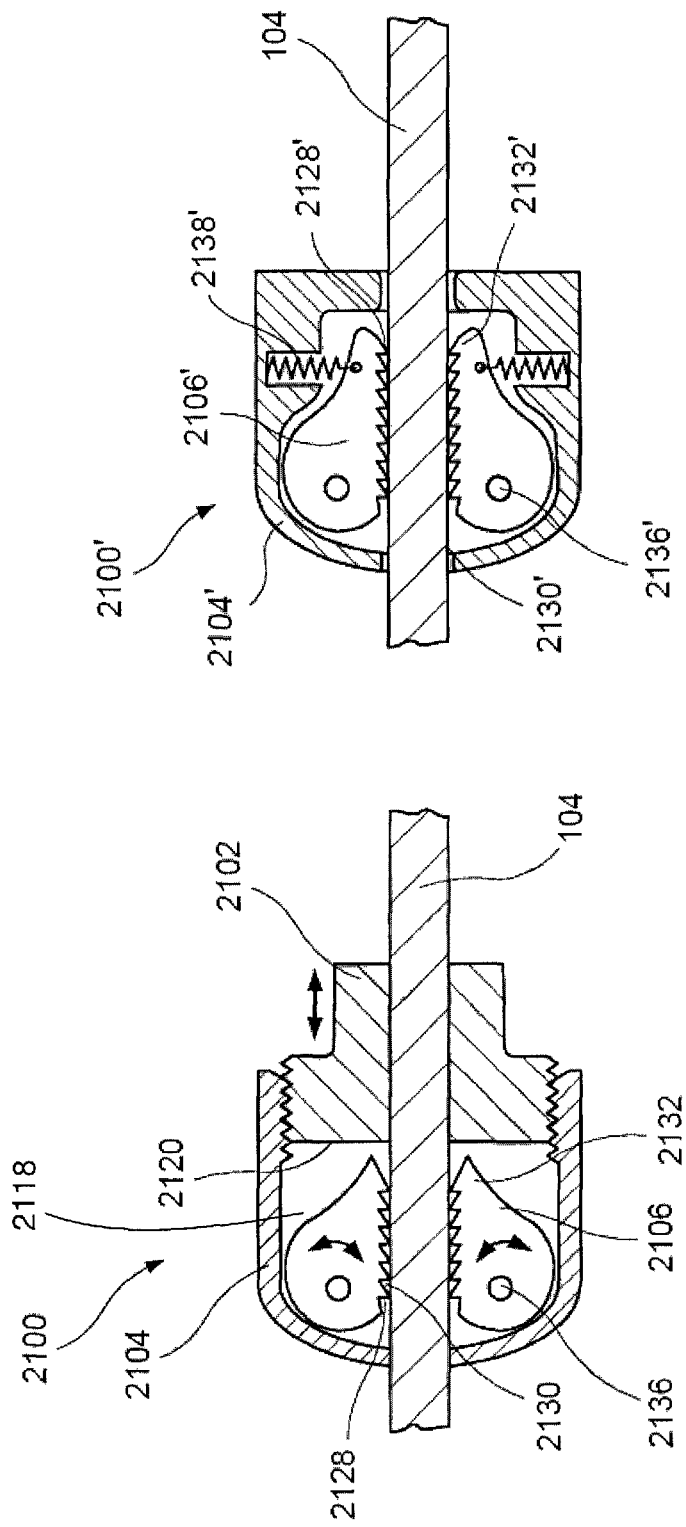
FIG. 58 shows a cross-sectional side view of a cable fixation device according to a twenty first exemplary embodiment of the present invention.
FIG. 59 shows a cross-sectional side view of an alternate embodiment of the cable fixation device of FIG. 58.

As shown in FIG. 58, a cable fixation device 2100 may be substantially similar to the cable fixation device 2000, as described above. The cable fixation device 2100 comprises a clamp 2102 and a clamping ring 2104 that are movably coupled to one another. Rather than the lever 2006, however, the cable fixation device 2100 further comprises a pair of wings 2106 that are movable between a first configuration, in which the wings 2106 do not grip the cable 104' passing through the cable fixation device 2100, to a second configuration, in which the pair or wings 2106 pivot to grip the cable 104 therebetween.

Similarly to the device 2000, the pair of wings is substantially housed within the clamping ring 2104. However, rather than being pivotably coupled to the clamp 2102, each of the wings 2106 are pivotably coupled to the clamping ring 2104 via a pin 2136 extending laterally through the clamping ring 2104 through the wing 2106, allowing the wings 2106 to pivot relative to the clamping ring 2104. Each of the wings 2106 are positioned on opposing sides of a lumen 2118 of the clamping ring 2104 such that the cable 104 is slidable between a space 2128 between each of the wings 2106. The wings 2106 further include ridges 2130 or teeth that are capable of gripping the cable 104 in the second configuration.

The cable fixation device 2100 may be positioned such that the clamping 2104 is positioned distally of the clamp 2102. Thus, a proximal end 2132 of the pair of wings 2106 faces a distal surface 2120 of the clamp 2102. In the first configuration, the distal surface 2120 of the clamp 2102 does not contact the proximal end 2132 of the wings 2106. In the second configuration, however, the clamp 2102 is moved relative to the clamping ring 2104 such that the distal surface 2120 of the clamp 2102 comes into contact with the proximal end 2132 of the pair of wings 2106, pushing the proximal end 2132 such that the pair of wings 2106 pivot to grip the cable 104 between each of the ridges 2130, thereby fixing the cable fixation device 2100 over a desired position along the cable 104.

According to an alternate embodiment, as shown in FIG. 59, a cable fixation device 2100' is substantially similar to the cable fixation device 2100, but does not include a clamp 2102. Rather, the cable fixation device 2100' comprises a clamping ring 2104' in which a pair of wings 2106' is substantially housed within. The pair of wings 2106' are pivotably coupled to the clamping ring 2104' via pins 2136'. In addition, each of the proximal ends 2132' of the wings 2106' are connected to the clamping ring 2104' via a spring 2138' such that the pair of wings 2106' may pivot laterally within the clamping ring 2104' via a tensioning and compressing of the spring 2138'. It will be understood by those of skill in the art that the spring 2138' biases the pair of wings 2106' toward a closed clamping configuration.

As the cable 104 is inserted proximally through a space 2128' between the pair of wings 2106', the spring 2138' compresses to accommodate the cable 104 therebetween. The cable fixation device 2100' may be slid along the cable 104 to a desired position along the cable 104. Once the cable fixation device 2100' has been positioned as desired, the cable 104 will be prevented from moving distally relative to the clamping ring 2104' since the springs 2138' provide a tension, which will maintain the pair of wings 2106' in the closed configuration in which ridges 2130' grip the cable 104 passing therebetween.

Figure 60:
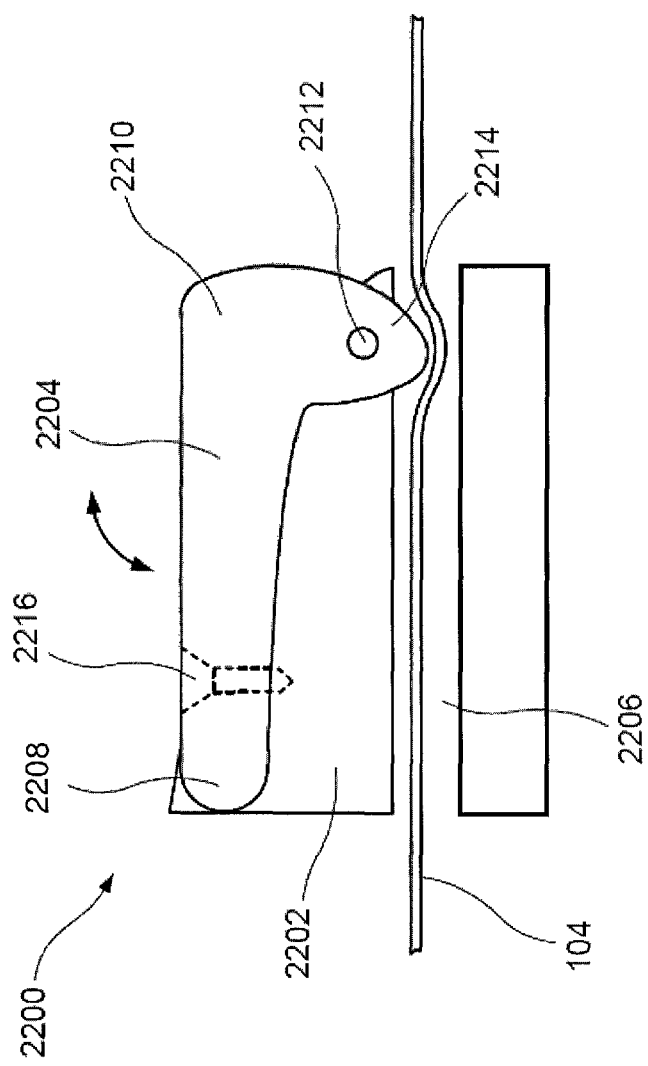
FIG. 60 shows a cross-sectional side view of a cable fixation device according to a twenty second exemplary embodiment of the present invention.

As shown in FIG. 60, a cable fixation device 2200 comprises a body 2202 and a lever 2204 that is pivotably coupled to the body 2202. The body 2202 include a lumen 2206 extending therethrough, the lumen 2206 being sized and shaped to accommodate the cable 104. The lever 2204 may extend substantially longitudinally from a first end 2208 to a second end 2210. The second end 2210 may be coupled to the body 2202 via a pin 2212, which permits the lever 2204 to pivot about the pin 2212 relative to the body 2202. The lever 2204 may pivot from a first configuration in which the lever 2204 is substantially perpendicular to a longitudinal axis of the body 2202 to a second configuration in which the lever 2204 is substantially parallel to the longitudinal axis.

The lever 2204 further includes a protrusion 2214 protruding laterally from the second end 2210 of the lever 2204. When the lever 2204 is in the first configuration, the protrusion 2214 does not extend into the lumen 2206. However, when the lever 2204 is moved to the second configuration, the protrusion does extend into the lumen 2206 such that the protrusion 2214 clamps the cable 104 passing therethrough, fixing the cable fixation device 2200 in a desired position along the cable 104. In a further embodiment, the cable fixation device 2200 may also comprise a screw 2216 of other insert that may fix the lever 2204 to the body 2202 in the second configuration, preventing the lever 2204 from being inadvertently moved to the first configuration to release the cable 104.

It will be apparent to those of skill in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:
1. A cable fixation device, comprising:
a clamp including a lumen extending therethrough, a longitudinal axis of the lumen being parallel to a longitudinal axis of the device; and
a clamping ring including a channel extending therethrough, the channel including a first portion and a second portion, the first portion being sized and shaped to slidably accommodate a cable therethrough and the second portion being sized and shaped to engage with a portion of the clamp, the clamp and the clamping ring movable relative to one another between a first configuration and a second configuration, the lumen and the channel substantially co-axial in the first configuration and off-set from one another in the second configuration, crushing the cable passing therebetween, wherein the clamp is rotated relative to the clamping ring about a longitudinal axis thereof to move the clamp into the second configuration and wherein the clamp and the clamping ring engage one another via an insert that is insertable into an opening in the clamping ring and a corresponding opening of the clamp, fixing the clamp and the clamping ring relative to one another and in the second configuration.

2. A cable fixation device, comprising:
a clamp including a lumen extending therethrough, the lumen sized and shaped to slidably accommodate a cable therethrough;
a clamping ring including a channel extending therethrough, the channel including a first portion and a second portion, the first portion sized and shaped to slidably accommodate the cable and the second portion sized and shaped to accommodate at least a portion of the clamp; and
a damper housed substantially within the second portion of the channel of the clamping ring and received within a recess extending through a portion of the clamp, the damper being movable between a first configuration, in which the damper is radially outward of the first portion, and a second configuration, in which the damper is moved radially inward by a portion of the clamp such that the cable passing through the channel is clamped by the damper.

3. The cable fixation device of claim 2, wherein the damper includes a plurality of spheres such that the cable passes therebetween.

4. The cable fixation device of claim 2, wherein the damper includes a single sphere that is movable from the first configuration to the second configuration.

5. The cable fixation device of claim 2, wherein the damper includes a longitudinal element that is movable between the first configuration and the second configuration.

6. The cable fixation device of claim 2, wherein the recess extends through a distal end of the clamp, the recess including an angled surface that contacts the damper to move the damper from the first configuration to the second configuration.

7. A cable fixation device, comprising:
a clamp including a lumen extending therethrough, the lumen sized and shaped to slidably accommodate a cable therethrough;
a housing including a channel extending therethrough, the channel including a first portion and a second portion, the first portion sized and shaped to slidably accommodate the cable and the second portion sized and shaped to accommodate at least a portion of the clamp; and
a clamp member within the housing including a plurality of contacting surfaces facing radially inward toward an opening, the clamp member being biased toward an open configuration, in which the contacting surfaces are separated from a center of the opening so that the opening is sized and shaped to slidably receive the cable therethrough, movement of the housing relative to the clamp bringing the clamp into contact with the clamp member and moving the clamp member from the open configuration to a closed configuration in which the contacting surfaces lockingly engage the cable to fix a position of the cable fixation device relative to the cable.

8. The cable fixation of claim 7, wherein the clamp member is substantially disc-shaped.

9. The cable fixation device of claim 7, wherein the clamp member is a zig-zag shape such that the opening passes through portions of the clamp member separated from one another along a length of a cable extending therethrough.

10. A cable fixation device, comprising:
a clamp body including a first lumen extending therethrough sized and shaped to slidably accommodate a cable and a second lumen, a distal end of which, is open to a portion of the first lumen distal of a proximal end thereof; and
a clamp sized and shaped for insertion into one of the first and second lumens to lockingly engage a portion of a cable at the distal end of the second lumen, the clamp being lockable within the one of the first and second lumens to maintain the cable at the desired position within the clamp body, wherein the clamp is locked within the one of the first and second lumens by a lock member slidable in a third lumen open to the second lumen, a distal end of the lock member engaging a corresponding feature of the clamp.

11. A cable fixation device, comprising:
a clamp including a lumen extending therethrough, the lumen sized and shaped to slidably accommodate a cable therethrough;
a clamping ring including a channel extending therethrough, the channel including a first portion and a second portion, the first portion sized and shaped to slidably accommodate the cable and the second portion sized and shaped to accommodate at least a portion of the clamp; and
a sheet housed substantially within the second portion of the channel of the clamping ring and including an opening extending therethrough, the sheet being movable between a first configuration, in which the opening is substantially coaxial with a longitudinal axis of the cable fixation device, and a second configuration, in which the opening is angled relative to the longitudinal axis such that the cable passing through the channel is clamped by an inner surface of the opening.

* * * * *